United States Patent
Hirota et al.

(10) Patent No.: US 9,523,664 B2
(45) Date of Patent: Dec. 20, 2016

(54) POWDER DETECTOR, IMAGE FORMING APPARATUS INCLUDING SAME, AND POWDER DETECTING METHOD

(71) Applicants: Tetsuro Hirota, Kanagawa (JP); Kenji Kikuchi, Kanagawa (JP); Hiroshi Hosokawa, Kanagawa (JP)

(72) Inventors: Tetsuro Hirota, Kanagawa (JP); Kenji Kikuchi, Kanagawa (JP); Hiroshi Hosokawa, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/884,961

(22) Filed: Oct. 16, 2015

(65) Prior Publication Data

US 2016/0116860 A1 Apr. 28, 2016

(30) Foreign Application Priority Data

Oct. 23, 2014 (JP) ................ 2014-216558
Oct. 23, 2014 (JP) ................ 2014-216559

(51) Int. Cl.
*G03G 15/00* (2006.01)
*G01N 33/00* (2006.01)
*G01M 7/02* (2006.01)
*G03G 15/08* (2006.01)

(52) U.S. Cl.
CPC .............. *G01N 33/00* (2013.01); *G01M 7/02* (2013.01); *G03G 15/086* (2013.01); *G03G 15/0858* (2013.01); *G01N 2033/0091* (2013.01)

(58) Field of Classification Search
USPC ........ 399/9, 24, 27–30, 107, 110, 111, 119, 399/120, 252, 258, 262
See application file for complete search history.

(56) References Cited

U.S. PATENT DOCUMENTS

| 5,438,393 A | 8/1995 | Komatsu et al. |
| 7,499,656 B2 * | 3/2009 | Kimura .............. G03G 15/0853 399/27 |
| 8,405,878 B2 * | 3/2013 | Kang ................... H04N 1/4055 358/3.06 |
| 8,543,014 B2 * | 9/2013 | Kobuse ................ G03G 15/553 399/110 |
| 2003/0235233 A1 | 12/2003 | Kawakatsu |
| 2005/0226656 A1 | 10/2005 | Tsuda et al. |
| 2010/0003055 A1 | 1/2010 | Kikuchi et al. |

(Continued)

FOREIGN PATENT DOCUMENTS

| EP | 0 599 233 A1 | 6/1994 |
| EP | 1 376 076 A1 | 1/2004 |

(Continued)

OTHER PUBLICATIONS

Extended European Search Report issued Apr. 4, 2016 in Patent Application No. 15190816.7.

*Primary Examiner* — Hoan Tran
(74) *Attorney, Agent, or Firm* — Oblon, McClelland, Maier & Neustadt, L.L.P.

(57) ABSTRACT

A powder detector to detect an amount of powder in the powder container includes a vibration plate disposed in the powder container to vibrate, a contact member to vibrate the vibration plate; and a vibration detector to detect a vibration state of the vibration plate. The powder has flowability, and the vibration state of the vibration plate is affected by the powder in the powder container.

15 Claims, 17 Drawing Sheets

(56) References Cited

U.S. PATENT DOCUMENTS

| | | |
|---|---|---|
| 2010/0119264 A1 | 5/2010 | Yamaguchi et al. |
| 2011/0182626 A1 | 7/2011 | Hirota et al. |
| 2011/0222871 A1 | 9/2011 | Suzuki et al. |
| 2012/0063797 A1 | 3/2012 | Hirota et al. |
| 2013/0011166 A1 | 1/2013 | Yamaguchi et al. |
| 2013/0039670 A1 | 2/2013 | Hosoya et al. |
| 2013/0322927 A1 | 12/2013 | Matsumoto et al. |
| 2014/0119780 A1 | 5/2014 | Hori et al. |
| 2014/0270859 A1 | 9/2014 | Hosokawa et al. |
| 2014/0312886 A1 | 10/2014 | Hirota et al. |

FOREIGN PATENT DOCUMENTS

| | | |
|---|---|---|
| JP | 2005-195884 | 7/2005 |
| JP | 2013-037280 | 2/2013 |
| JP | 2013-156504 | 8/2013 |

* cited by examiner

| n | 0 | 1 | 2 | 3 | 4 | 5 | 6 | 7 | 8 | 9 | 10 | 11 | |
|---|---|---|---|---|---|---|---|---|---|---|----|----|---|
| $S_n$ | 3400 | 3390 | 3360 | 3340 | 3310 | 3300 | 3310 | 3320 | 3350 | 3370 | 3380 | 3370 | ... |
| $S_{n-1} - S_n$ | – | + | + | + | + | + | – | – | – | – | – | + | |

# POWDER DETECTOR, IMAGE FORMING APPARATUS INCLUDING SAME, AND POWDER DETECTING METHOD

CROSS-REFERENCE TO RELATED APPLICATIONS

This patent application is based on and claims priority pursuant to 35 U.S.C. §119(a) to Japanese Patent Application Nos. 2014-216558 and 2014-216559, both filed on Oct. 23, 2014, in the Japan Patent Office, the entire disclosure of each of which is hereby incorporated by reference herein.

BACKGROUND

Technical Field

Embodiments of the present invention relate to a powder detector, an image forming apparatus including the powder detector, and a powder detecting method.

Description of the Related Art

At present, use of information in the form of electronic data is increasing. Accordingly, printers and facsimile machines to output electronic data and image processing apparatus, such as scanners, to convert information into electronic data are widely used. Among such image processing apparatuses, there are apparatuses that employ electrophotography. In electrophotographic image formation, an electrostatic latent image formed on an image bearer such as a photoconductor is developed and transferred onto a recording medium such as a sheet of paper.

Electrophotographic image forming apparatuses typically include a developing device to develop the electrostatic latent image, and developer is supplied from a developer container to the developing device. The image forming apparatus includes a detector to detect the amount of developer remaining in the developing device or the developer container.

SUMMARY

An embodiment of the present invention provides a powder detector to detect an amount of powder stored in the powder container and having flowability. The powder detector includes a vibration plate disposed in the powder container to vibrate, a vibration detector to detect the vibration state of the vibration plate, a contact member to vibrate the vibration plate. The vibration state of the vibration plate is affected by the powder in the powder container, and the vibration detector outputs a detection result indicating the vibration state of the vibration plate.

Another embodiment provides an image forming apparatus includes an image forming unit to form an image, the powder container, and the powder detector described above. The power container contains a powder used by the image forming unit to form the image.

Yet another embodiment provides a powder detecting method to detect an amount of powder stored in a powder container and having flowability. The powder detecting method includes a step of vibrating a vibration plate disposed on the powder container, a step of detecting, with a vibration detector, the vibration state of the vibration plate; and a step of recognizing the amount of the powder in the powder container according to the vibration state detected. The vibration state of the vibration plate is affected by the powder in the powder container.

BRIEF DESCRIPTION OF THE SEVERAL VIEWS OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
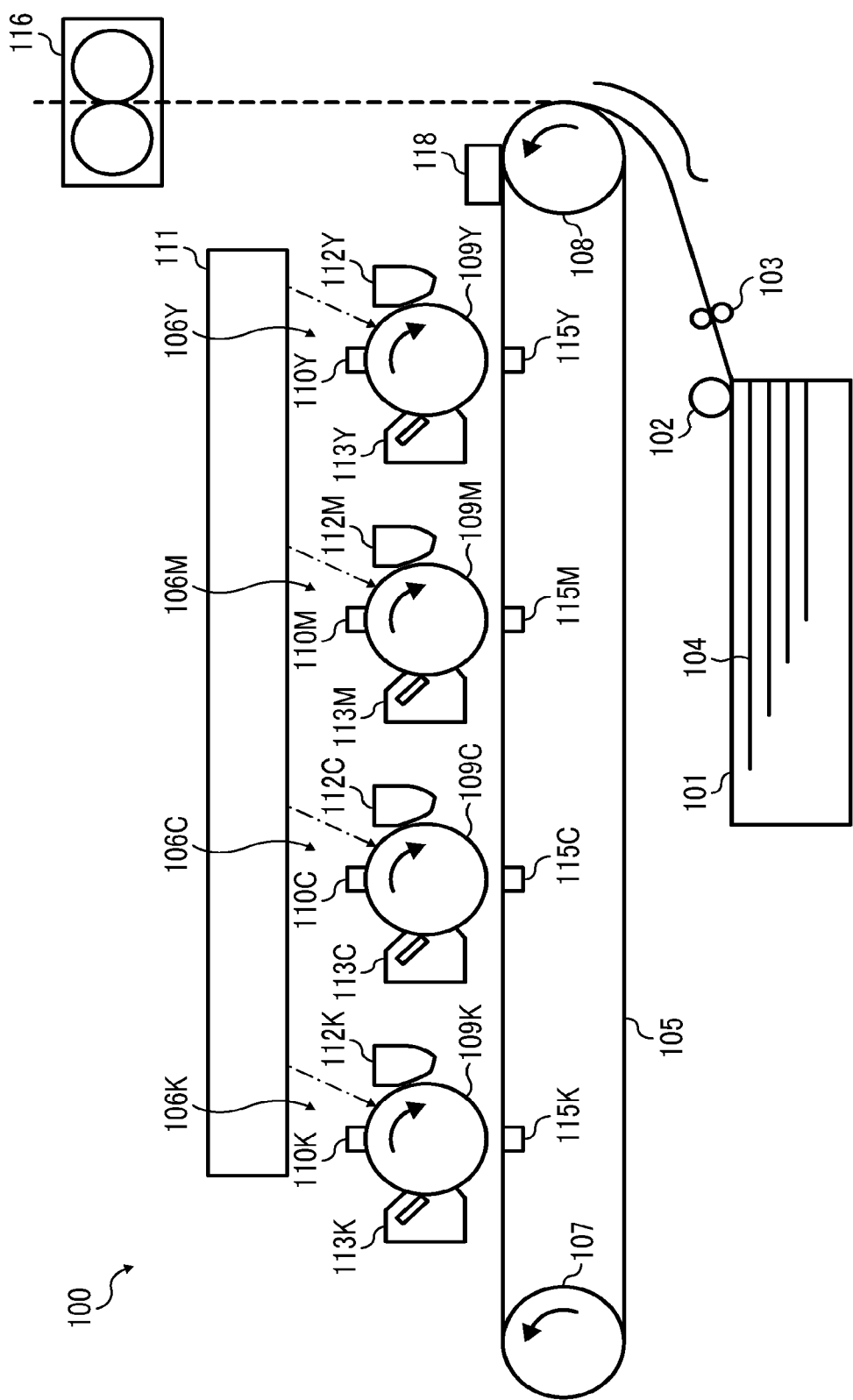
FIG. 1 illustrates a mechanical structure of an image forming apparatus including a developing device provided with a magnetic flux sensor according to an embodiment.

In describing preferred embodiments illustrated in the drawings, specific terminology is employed for the sake of clarity. However, the disclosure of this patent specification is not intended to be limited to the specific terminology so selected, and it is to be understood that each specific element includes all technical equivalents that operate in a similar manner and achieve a similar result.

Descriptions are given below of, as an embodiment of the present invention, detection of the amount of developer or toner remaining in an electrophotographic image forming apparatus, in particular, the amount of toner remaining in a sub-hopper to store toner in a portion between a developing device, which develops an electrostatic latent image on a photoconductor, and a container from which toner is supplied to the developing device.

Referring now to the drawings, wherein like reference numerals designate identical or corresponding parts throughout the several views thereof, and particularly to FIG. 1, a multicolor image forming apparatus according to an embodiment of the present invention is described.

The image forming apparatus 100 illustrated in FIG. 1 is a so-called tandem-type image forming apparatus and includes multiple image forming units 106K, 106C, 106M, and 106Y for respective colors, arranged along an endless conveyor belt 105. Specifically, the image forming units 106Y, 106M, 106C, and 106K (hereinafter collectively "image forming units 106"), serving as electrophotographic process units, are arranged in that order from the upstream side in the direction in which the conveyor belt 105 transports the image. In the image forming apparatus 100, sheets 104 of recording media are fed from a sheet feeding tray 101 by a sheet feeding roller 102. The conveyor belt 105 is an intermediate transfer belt, and an intermediate transfer image to be transferred onto the sheet 104 is formed on the conveyor belt 105.

Additionally, a registration roller pair 103 stops the sheet 104 fed from the sheet feeding tray 101 and forwards the sheet 104 to a secondary transfer position where the image is transferred from the conveyor belt 105, timed to coincide with image formation in the image forming units 106.

The multiple image forming units 106 is similar in configuration except the color of toner images formed thereby. The image forming unit 106K forms black toner images, the image forming unit 106M forms magenta toner images, the image forming unit 106C forms cyan toner images, and the image forming unit 106Y forms yellow toner images. It is to be noted that the image forming unit 106Y is described in detail below as a representative since the image forming units 106Y, 106M, 106C, and 106K are similar in structure. Thus, and descriptions of other image forming units 106M, 106C, and 106K, given subscripts "M", "C", and "K", instead of "Y" in the drawings, are omitted.

The conveyor belt 105 is an endless belt entrained around a driving roller 107 and a driven roller 108. A driving motor rotates the driving roller 107. The driving motor, the driving roller 107, and the driven roller 108 together constitute a driving unit to drive the conveyor belt 105.

Among the four image forming units 106, initially the image forming unit 106Y transfers toner images onto the conveyor belt 105. The image forming unit 106Y includes a photoconductor drum 109Y and components disposed around the photoconductor drum 109Y, namely, a charging device 110Y, an optical writing device 111, a developing device 112Y, a photoconductor cleaner 113Y, and a discharger. The optical writing device 111 directs light to the photoconductor drum 109Y, 109M, 109C, and 109K (collectively "photoconductor drums 109").

To form images, the charging device 110Y charges uniformly the outer circumferential face of the photoconductor drum 109Y in the dark, after which the optical writing device 111 directs light from a light source corresponding to yellow images to the photoconductor drum 109Y, thus forming an electrostatic latent image thereon. The developing device 112Y develops the electrostatic latent image with yellow toner, thus forming a yellow toner image on the photoconductor drum 109Y.

The toner image is transferred by a transfer device 115Y onto the conveyor belt 105 at a primary transfer position where the photoconductor drum 109Y contacts or is closest to the conveyor belt 105. Thus, the yellow toner image is formed on the conveyor belt 105. Subsequently, the photoconductor cleaner 113Y removes toner remaining on the outer circumferential face of the photoconductor drum 109Y, and the discharger discharges the outer circumferential face of the photoconductor drum 109Y. Then, the photoconductor drum 109Y is on standby for subsequent image formation.

The yellow toner image formed on the conveyor belt 105 by the image forming unit 106Y is then transported to the image forming unit 106M as the conveyor belt 105 is rotated by the rollers. The image forming unit 106M performs image forming processes similar to those performed by the image forming unit 106Y, thereby forming a magenta toner image on the photoconductor drums 109M, and the magenta toner image is transferred and superimposed on the yellow toner image.

The yellow and magenta toner images on the conveyor belt 105 are further transported to the image forming units 106C and 106K, where cyan and black toner images are formed on the photoconductor drums 109C and 109K, respectively, and the cyan and black toner images are transferred on the superimposed toner image on the conveyor belt 105. Thus, a multicolor intermediate toner image is formed on the conveyor belt 105.

The sheets 104 contained in the sheet feeding tray 101 are sent out from the top sequentially. At a position where a conveyance path leading therefrom contacts or is closest to the conveyor belt 105, the intermediate toner image is transferred from the conveyor belt 105 onto the sheet 104. Thus, an image is formed on the sheet 104. The sheet 104 carrying the image is transported to a fixing device 116, where the image is fixed on the sheet 104. Then, the sheet 104 is ejected outside the image forming apparatus 100.

The conveyor belt 105 is provided with a belt cleaner 118. The belt cleaner 118 includes a cleaning blade pressed against the conveyor belt 105 to scrape off toner from the surface of the conveyor belt 105 at a position downstream from the secondary transfer position and upstream from the photoconductor drums 109 in the direction in which the conveyor belt 105 rotates (in the direction of rotation of the driving roller 107 and the driven roller 108) as illustrated in FIG. 1. Thus, the belt cleaner 118 serves as a developer remover.

Figure 2:
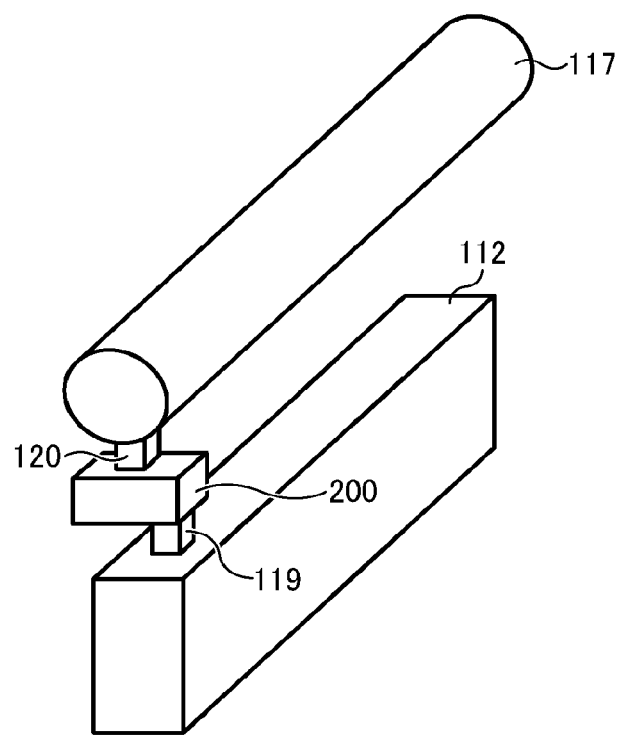
FIG. 2 is a perspective view illustrating a configuration for toner supply according to an embodiment.

Referring to FIG. 2, descriptions are given below of structures for toner supply to the developing devices 112, which are similar among cyan (C), magenta (M), yellow (Y), and black (K) toners. Thus, FIG. 2 illustrates the structure to supply one of the four toners. In FIG. 2, a first toner supply passage 119 extends from a sub-hopper 200 to the developing device 112, and a second toner supply passage 120 extends from the toner bottle 117 to the sub-hopper 200. Toner contained in the toner bottle 117 is supplied through the second toner supply passage 120 to the sub-hopper 200.

The sub-hopper 200 temporarily stores toner supplied from the toner bottle 117 and supplies the toner to the developing device 112 according to the amount of toner remaining in the developing device 112. From the sub-hopper 200, toner is supplied through the first toner supply passage 119 to the developing device 112. When no or almost no toner remains in the toner bottle 117, toner is not supplied to the sub-hopper 200. An aspect of the present embodiment is to recognize that the amount of toner remaining in the sub-hopper 200 is small.

Figure 3:
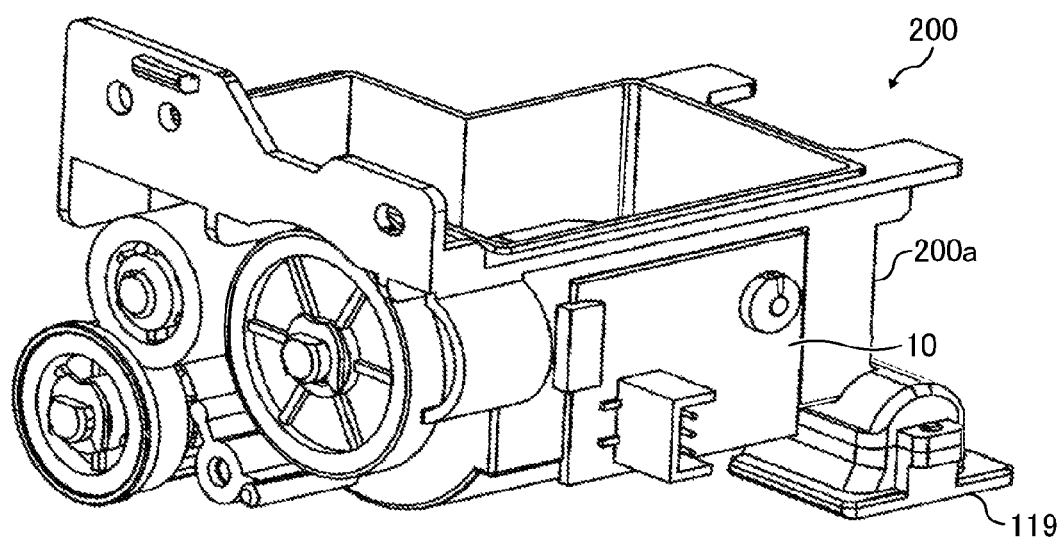
FIG. 3 is a perspective view illustrating an exterior of a sub-hopper according to an embodiment.

FIG. 3 is a perspective view illustrating an exterior of the sub-hopper 200 according to the present embodiment.

As illustrated in FIG. 3, a magnetic flux sensor 10 is secured to an outer wall of a housing 200a of the sub-hopper 200. In FIG. 3, an upper side of the sub-hopper 200 is open, and a cover, which communicates with the second toner supply passage 120, is attached to the open side of the sub-hopper 200. Toner is discharged from the sub-hopper 200 through the first toner supply passage 119.

Figure 4:
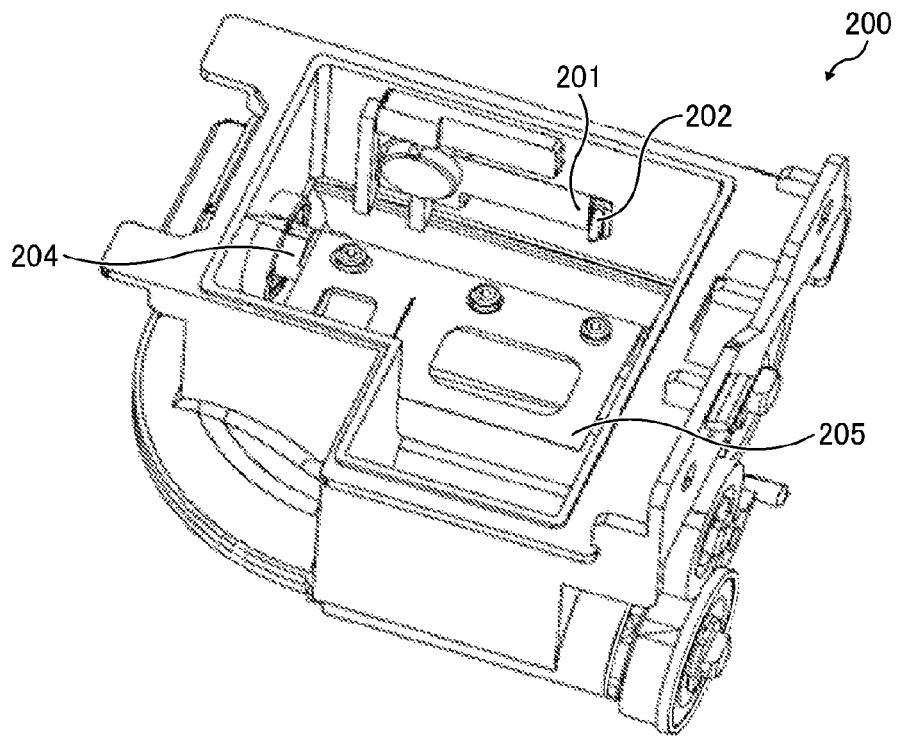
FIG. 4 is another perspective view illustrating the exterior of the sub-hopper illustrated in FIG. 3.

FIG. 4 is a perspective view illustrating an interior of the sub-hopper 200 according to the present embodiment. As illustrated in FIG. 4, a vibration plate 201 is secured to an inner wall of the sub-hopper 200. Specifically, the vibration plate 201 is secured to the inner wall on the back of the magnetic flux sensor 10 secured to the outer wall of the housing 200a in FIG. 3. Accordingly, the vibration plate 201 is disposed facing the magnetic flux sensor 10.

The vibration plate 201 is planar and rectangle in the present embodiment. A first end of a long side of the vibration plate 201 is secured to the housing 200a of the sub-hopper 200, and a second end of the vibration plate 201 is not secured. Thus, the vibration plate 201 is cantilevered by the housing 200a. Additionally, a projection 202, serving as a weight as well as a contact portion, is disposed at the second end of the long side of the vibration plate 201.

The projection 202 is used for vibrating the vibration plate 201 and for adjusting the vibration frequency when the vibration plate 201 vibrates.

A shaft 204 and an agitator 205 are disposed inside the sub-hopper 200 to stir the toner contained therein. The shaft 204 rotates inside the sub-hopper 200. The agitator 205 is secured to the shaft 204. As the shaft 204 rotates, the agitator 205 stirs, by rotation, the toner contained inside the sub-hopper 200. A longitudinal direction of the vibration plate 201 substantially is arranged substantially parallel to the axial direction of the shaft 204.

The agitator 205 has a capability to flip, by rotation, the projection 202 provided to the vibration plate 201 in addition to toner stirring capability. Each time the agitator 205 makes one rotation, the agitator 205 flips the projection 202, and the vibration plate 201 vibrates. In other words, the agitator 205 serves as a contact member to contact the vibration plate 201, and the vibration plate 201 vibrates due to the contact with the agitator 205. An aspect of the present embodiment is to detect the vibration of the vibration plate 201, thereby detecting the amount of toner remaining inside the sub-hopper 200.

Next, descriptions are given below of an internal structure of the magnetic flux sensor 10 according to the present embodiment with reference to FIG. 5.

Figure 5:
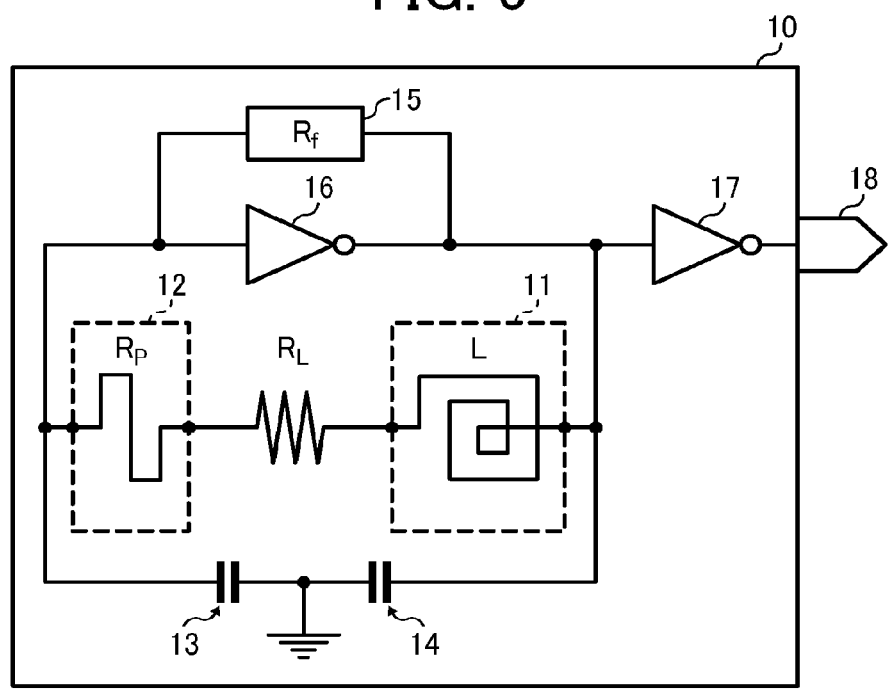
FIG. 5 illustrates circuitry of a magnetic flux sensor according to an embodiment.

As illustrated in FIG. 5, the magnetic flux sensor 10 is an oscillator circuit based on a Colpitts-type LC oscillator circuit and includes a coil pattern 11, a resistor pattern 12, first and second capacitors 13 and 14, a feedback resistor 15 having a resistance value $R_f$, unbuffered integrated circuits (ICs) 16 and 17, and an output terminal 18. It is to be noted that reference character "$R_L$" represents circuit resistance caused by conducting wire (signal wire) forming the circuit illustrated in FIG. 5.

The coil pattern 11 is a planar coil made from conducting wire (signal wire) printed on a board 300 (illustrated in FIG. 7) of the magnetic flux sensor 10. As illustrated in FIG. 5, the coil pattern 11 has an inductance L attained by the coil. In the coil pattern 11, the inductance L changes depending on the magnetic flux passing through a space opposing a board face on which the coil pattern 11 is printed. The magnetic flux sensor 10 in the present embodiment is used as a signal oscillator to output a signal having a frequency corresponding to the magnetic flux passing through the space opposed to the board face bearing the coil pattern 11.

Similar to the coil pattern 11, the resistor pattern 12 is a planar resistor made of a planar pattern of conducting wire printed on the board 300. The resistor pattern 12 in the present embodiment has a serpentine or zigzag pattern, thereby better inhibiting flow of electrical current compared with a resistor having a linear pattern. Incorporating the resistor pattern 12 is one aspect of the present embodiment. The term "zigzag" means the shape in which the wire is bent and folded back, like a serpentine, multiple times to reciprocate in a predetermined direction. Referring to FIG. 5, the resistor pattern 12 has a resistance value $R_p$. The coil pattern 11 and the resistor pattern 12 are connected in series with each other.

The first and second capacitors 13 and 14 serve as a capacitance and a part of the Colpitts-type LC oscillator circuit including the coil pattern 11. Accordingly, the first and second capacitors 13 and 14 are connected serially with the coil pattern 11 and the resistor pattern 12. A loop including the coil pattern 11, the resistor pattern 12, and the first and second capacitors 13 and 14 serves as a resonance current loop.

The feedback resistor 15 is inserted to stabilize a bias voltage. With a function of the unbuffered ICs 16 and 17, fluctuations in potential of a part of the resonance current loop are output as a rectangular wave corresponding to the resonance frequency from the output terminal 18.

With this configuration, the magnetic flux sensor 10 oscillates at a frequency f corresponding to the inductance L, the resistance value $R_P$, and a capacitance C of the first and second capacitors 13 and 14. The frequency f is expressed by Formula 1 below.

$$f = \frac{1}{2\pi}\sqrt{\frac{1}{LC} - \left(\frac{R_L + R_P}{2L}\right)^2} \qquad \text{Formula 1}$$

It is to be noted that the circuit resistance $R_L$ (resistance value) is determined by the length of the conducting wire, and most of the conducting wire is used to form the coil in the magnetic flux sensor 10 according to the present embodiment. Accordingly, the circuit resistance $R_L$ is substantially identical to the resistance value attained by the conducting wire forming the coil.

The inductance L changes depending on the presence and density of the magnetic material adjacent to the coil pattern 11 (planar coil). Thus, according to the oscillation frequency of the magnetic flux sensor 10, the magnetic permeability in the space adjacent to the coil pattern 11 can be determined.

As described above, the magnetic flux sensor 10 faces the vibration plate 201 via the housing 200a of the sub-hopper 200 in the present embodiment. Accordingly, the magnetic flux generated by the coil pattern 11 passes through the vibration plate 201. That is, the vibration plate 201 affects the magnetic flux generated by the coil pattern 11 and further affects the inductance L. Consequently, the vibration plate 201 affects the frequency of signal of the magnetic flux sensor 10, which is an aspect of the present embodiment.

Figure 6:
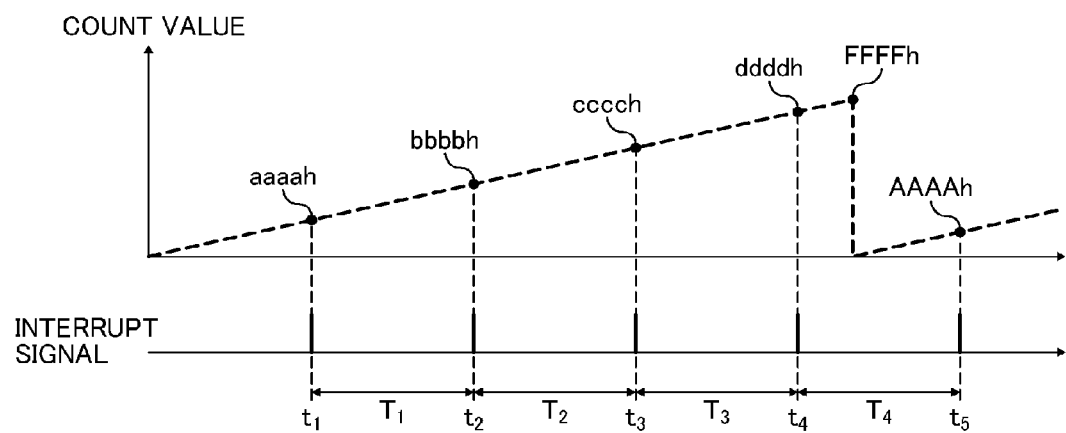
FIG. 6 is a chart of counting of signal output from the magnetic flux sensor illustrated in FIG. 5.

FIG. 6 is a chart of counting of signal output from the magnetic flux sensor 10 according to the present embodiment.

If the magnetic flux generated by the coil pattern 11 does not change, the magnetic flux sensor 10 keeps oscillating at a constant frequency basically. Consequently, the count value of the signal of the magnetic flux sensor 10 increases constantly with elapse of time as illustrated in FIG. 6, and, at Time points $t_1$, $t_2$, $t_3$, $t_4$, and $t_5$, count values aaaah, bbbbh, ccch, ddddh, and AAAAh are acquired respectively as illustrated in FIG. 6.

By calculating the count values at those timings based on Periods $T_1$, $T_2$, $T_3$, and $T_4$ in FIG. 6, respectively, the frequency in each of Periods $T_1$, $T_2$, $T_3$, and $T_4$ in FIG. 6 is calculated. For example, in a case where an interrupt signal is output each time a reference clock equivalent for 2 milliseconds (ms) is counted, the count value in each of Periods $T_1$, $T_2$, $T_3$, and $T_4$ illustrated in FIG. 6 is divided with 2 (ms), thereby calculating the frequency f (Hz) of the magnetic flux sensor 10 in that period.

Additionally, when the upper limit of the count value is FFFFh as illustrated in FIG. 6, the oscillation frequency f (Hz) in Period $T_4$, can be calculated by dividing, with 2 (ms), the sum of the AAAAh and a value obtained by deducting ddddh from FFFFh.

Thus, the image forming apparatus 100 according to the present embodiment acquires the frequency of signal generated by the magnetic flux sensor 10 and determines, based on the result of acquisition, a phenomenon corresponding to the oscillation frequency of the magnetic flux sensor 10. In the magnetic flux sensor 10 according to the present embodiment, the inductance L changes in response to the state of the vibration plate 201 disposed facing the coil pattern 11, and the frequency of signal output from the output terminal 18 changes accordingly.

Consequently, a controller 20 (illustrated in FIG. 8) to acquire the signal recognizes the state of the vibration plate 201 disposed facing the coil pattern 11. An aspect of the present embodiment is to detect the state of developer inside the sub-hopper 200 based on the state of the vibration plate 201.

It is to be noted that, although the frequency is obtained by dividing the count value of the signal by the period in the description above, alternatively, in a case where the period during which the count value is acquired is fixed, the acquired count value can be used as is as the parameter indicating the frequency.

Figure 7:
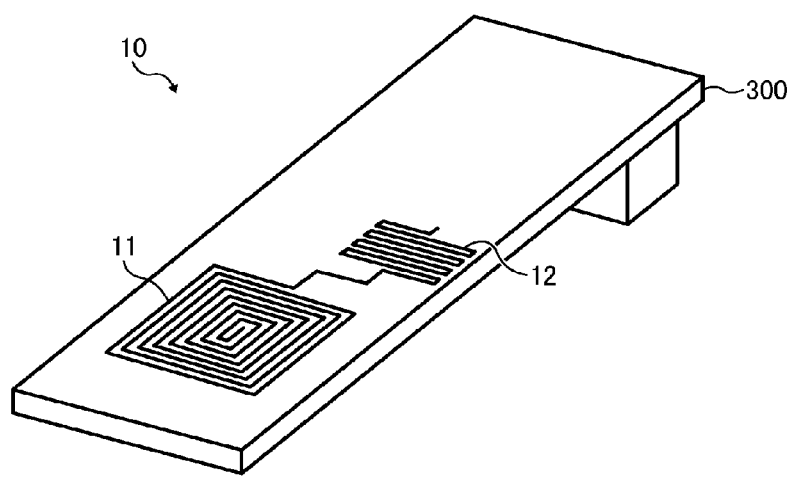
FIG. 7 is a perspective view illustrating an exterior of the magnetic flux sensor illustrated in FIG. 5.

FIG. 7 is a perspective view illustrating an exterior of the magnetic flux sensor 10 according to the present embodiment. In FIG. 7, the face of the board 300 on which the coil pattern 11 and the resistor pattern 12 are formed is faced up. That is, a detection face for detecting magnetic permeability, which is to oppose the space subjected to magnetic permeability detection, is faced up.

As illustrated in FIG. 7, the resistor pattern 12, which is connected serially to the coil pattern 11, is printed on the detection face on which the coil pattern 11 is printed. As described above with reference to FIG. 5, the coil pattern 11 is made of conducting wire (signal line) printed in a spiral shape on the board face. Additionally, the resistor pattern 12 is made of conducting wire printed in a serpentine or zigzag pattern on the board face, and the above-described function of the magnetic flux sensor 10 is established by these patterns.

The coil pattern 11 and the resistor pattern 12 serves as a detecting portion of the magnetic flux sensor 10 according to the present embodiment. The magnetic flux sensor 10 is attached to the sub-hopper 200 with the detecting portion facing the vibration plate 201.

Next, descriptions are given below of a structure to acquire outputs from the magnetic flux sensor 10 in the image forming apparatus 100 according to the present embodiment, with reference to FIG. 8.

Figure 8:
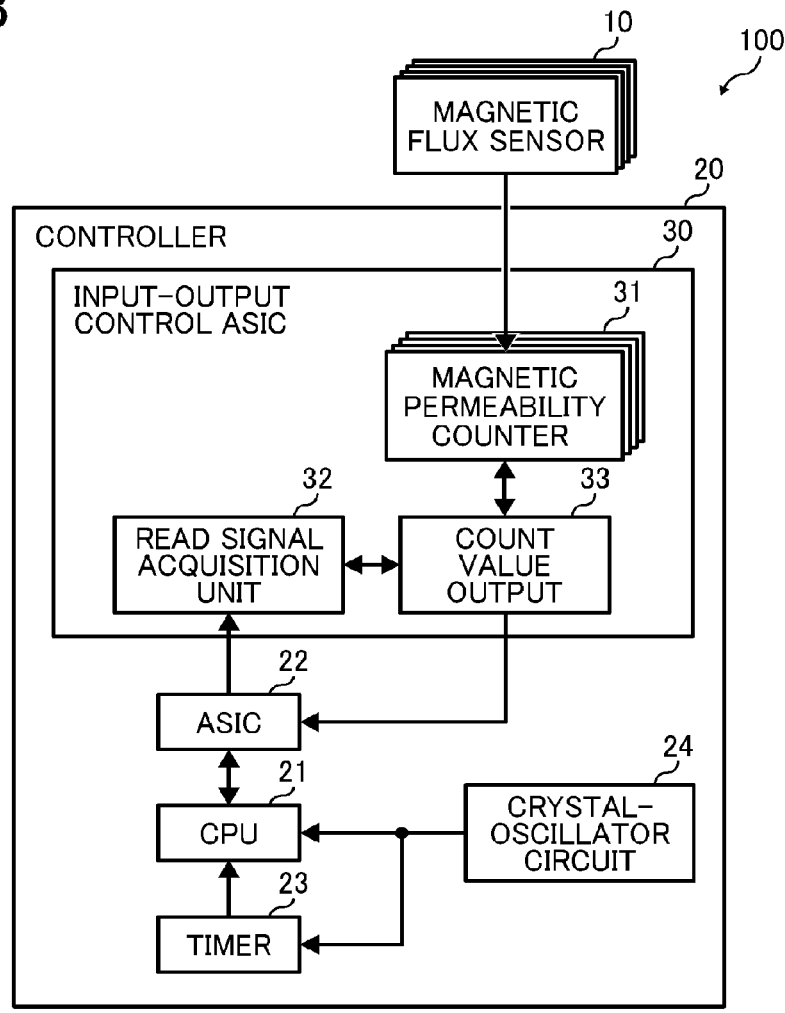
FIG. 8 is a block diagram illustrating a control configuration to acquire the signal output from the magnetic flux sensor illustrated in FIG. 5.

FIG. 8 is a schematic block diagram of the controller 20 to acquire the signal from the magnetic flux sensor 10. The controller 20 includes a central processing unit (CPU) 21, an application specific integrated circuit (ASIC) 22, a timer 23, a crystal-oscillator circuit 24, and an input-output control ASIC 30.

The CPU 21 is a computation unit and controls operation of the entire controller 20 by computation according to programs stored in a memory such as a read only memory (ROM). The ASIC 22 functions as a connection interface between a system bus, to which the CPU 21 and a random access memory (RAM) are connected, and another device.

The timer 23 outputs an interrupt signal to the CPU 21 each time the count of reference clock input from the crystal-oscillator circuit 24 reaches a predetermined count. In response to the interrupt signal input from the timer 23, the CPU 21 outputs the read signal for acquiring the output value of the magnetic flux sensor 10. The crystal-oscillator circuit 24 generates the reference clock to operate respective elements inside the controller 20.

The input-output control ASIC 30 acquires the signal output from the magnetic flux sensor 10 and converts the signals into data processable inside the controller 20. In the configuration illustrated in FIG. 8, the input-output control ASIC 30 includes a magnetic permeability counter 31, a read signal acquisition unit 32, and a count value output 33. As described above, the magnetic flux sensor 10 according to the present embodiment is an oscillator circuit that outputs a rectangular wave having the frequency corresponding to the magnetic permeability of the space as a detection target.

The magnetic permeability counter 31 increments the value according to the rectangular wave output from the magnetic flux sensor 10. That is, the magnetic permeability counter 31 serves as a target signal counter to count the number of the signal whose frequency is to be calculated. It is to be noted that, in the present embodiment, multiple magnetic flux sensors 10 are provided for the respective sub-hoppers 200 connected to developing devices 112Y, 112M, 112C, and 112K, and multiple magnetic permeability counters 31 are used accordingly.

The read signal acquisition unit 32 acquires, from the CPU 21 via the ASIC 22, the read signal, which is a command to acquire the count value of the magnetic permeability counter 31. Acquiring the read signal from the CPU 21, the read signal acquisition unit 32 inputs, to the count value output 33, a signal instructing output of the count value. According to the signal from the read signal acquisition unit 32, the count value output 33 outputs the count value of the magnetic permeability counter 31.

It is to be noted that the CPU 21 has an access to the input-output control ASIC 30, for example, via a register. Accordingly, the CPU 21 outputs the above-described read signal by writing a value in a predetermined register included in the input-output control ASIC 30. Additionally, the count value from the count value output 33 is stored in a predetermined register of the input-output control ASIC 30, from which the CPU 21 acquires the count value. The controller 20 illustrated in FIG. 8 is provided to an apparatus or a device other than the magnetic flux sensor 10 in one embodiment. In another embodiment, the controller 20 is mounted, as a circuit including the CPU 21, on the board 300 of the magnetic flux sensor 10.

In the above-described structure, the CPU 21 detects the vibration state of the vibration plate 201 based on the count value acquired from the count value output 33 and, based on the detection result, detects the amount of toner remaining in the sub-hopper 200. That is, a detection result processor is implemented by the CPU 21 performing computation according to a predetermined program. The count value acquired from the count value output 33 is used as frequency-related data indicating the frequency of the magnetic flux sensor 10, which changes corresponding to the vibration of the vibration plate 201.

Next, descriptions are given below of effects of the vibration plate 201 on the oscillation frequency of the magnetic flux sensor 10 according to the present embodiment.

Figure 9:
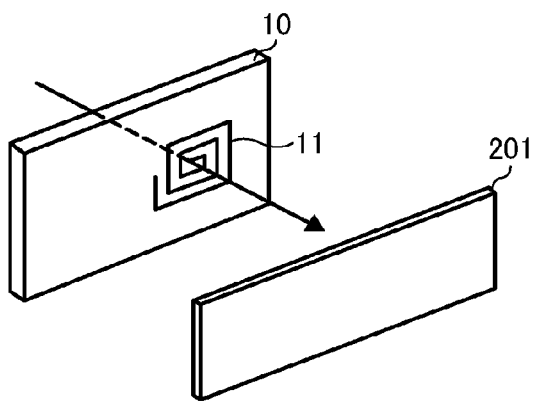
FIG. 9 illustrates a distance between the magnetic flux sensor and a vibration plate according to an embodiment.

Referring to FIG. 9, the board face of the magnetic flux sensor 10 bearing the coil pattern 11 faces the vibration plate 201 via the housing 200a of the sub-hopper 200 (illustrated in FIG. 3). Then, a magnetic flux arises, centering around a center of the coil pattern 11, and the magnetic flux penetrates the vibration plate 201.

Figure 10:
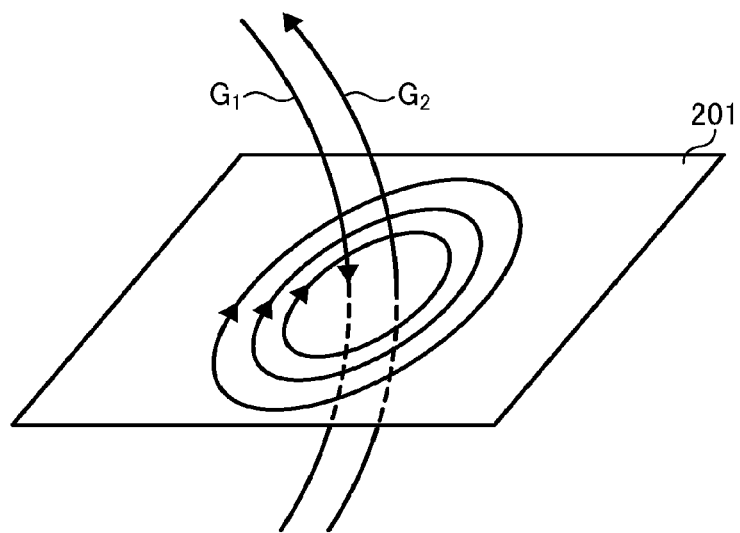
FIG. 10 illustrates actions of magnetic flux penetrating the vibration plate illustrated in FIG. 9.

For example, the vibration plate 201 is made of a plate of Steel Use Stainless (SUS) according to Japan Industrial Standard (JIS). As illustrated in FIG. 10, an eddy current is generated in the vibration plate 201 as a magnetic flux $G_1$ penetrates the vibration plate 201. A magnetic flux $G_2$ is generated by the eddy current and acts to cancel the magnetic flux $G_1$ generated by the coil pattern 11. As the magnetic flux $G_1$ is thus canceled, the inductance L in the magnetic flux sensor 10 decreases. As shown by Formula 1 above, the oscillation frequency f increases as the inductance L decreases.

Figure 11:
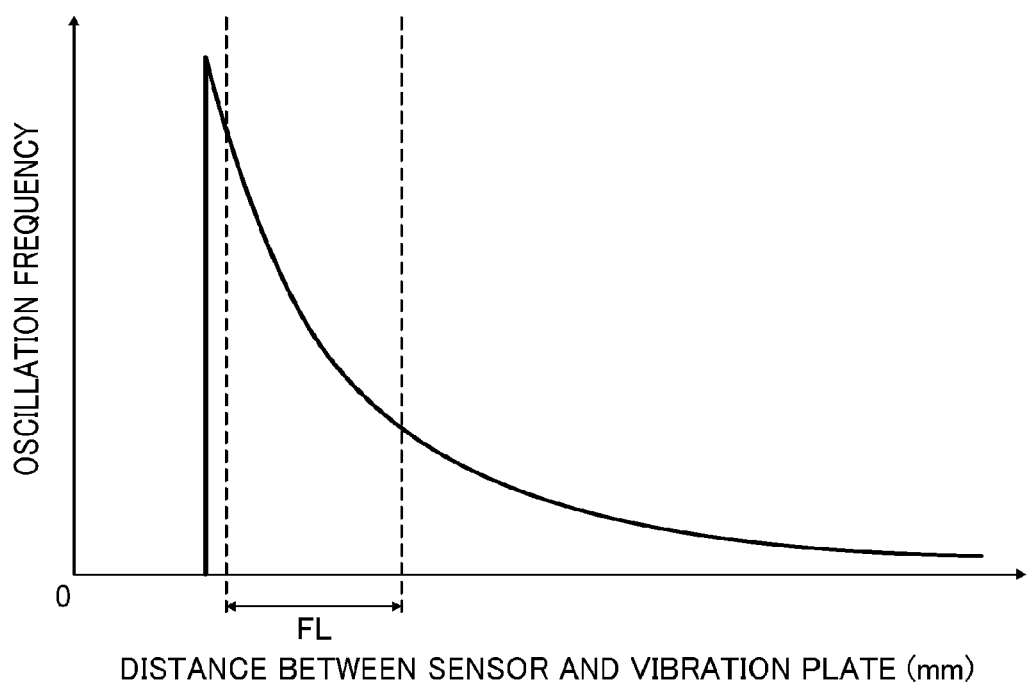
FIG. 11 is a graph of changes in oscillation frequency of the magnetic flux sensor corresponding to the distance between the magnetic flux sensor and the vibration plate.

The strength of the eddy current, which occurs inside the vibration plate 201 due to the magnetic flux generated by the coil pattern 11, changes according to the strength of the magnetic flux as well as a distance between the coil pattern 11 and the vibration plate 201. FIG. 11 is a graph of oscillation frequency of the magnetic flux sensor 10 corresponding to the distance between the coil pattern 11 and the vibration plate 201.

The strength of the eddy current occurring inside the vibration plate 201 is inversely proportional to the distance between the coil pattern 11 and the vibration plate 201. Accordingly, as the distance between the coil pattern 11 and the vibration plate 201 decreases, the oscillation frequency of the magnetic flux sensor 10 becomes higher. When the distance is smaller than a threshold, the inductance L is too low, and the magnetic flux sensor 10 does not oscillate. In FIG. 11, when the distance between the coil pattern 11 and the vibration plate 201 is in a range FL, the oscillation frequency changes steeply.

In the sub-hopper 200 according to the present embodiment, the CPU 21 detects the vibration of the vibration plate 201 by using characteristics illustrated in FIG. 11. The amount of toner remaining in the sub-hopper 200 is detected based on the vibration of the vibration plate 201 thus detected, which is an aspect of the present embodiment. In other words, the vibration plate 201 and the magnetic flux sensor 10 illustrated in FIG. 9 as well as the structure to process the signal output from the magnetic flux sensor 10 is used as a powder detector according to the present embodiment. The powder detector is used as a developer amount detector to detect the amount of developer (e.g., toner) remaining in the present embodiment. Additionally, the magnetic flux sensor 10 serves as a vibration detector.

The vibration of the vibration plate 201 flipped by the agitator 205 is expressed by an eigenfrequency defined by rigidity of the vibration plate 201 and weight of the projection 202, and an attenuation ratio defined by external factors to absorb the vibration energy. The external factors to absorb the vibration energy include, the presence of toner that contacts the vibration plate 201 in the sub-hopper 200, in addition to fixed factors such as the holding strength of the mount 201a cantilevering the vibration plate 201 and air resistance.

The amount or state of toner that contacts the vibration plate 201 changes depending on the amount of toner remaining in the sub-hopper 200. Accordingly, by detecting the vibration of the vibration plate 201, the amount of toner remaining in the sub-hopper 200 is detected. In the sub-hopper 200 according to the present embodiment, the agitator 205 to stir toner flips the vibration plate 201 and vibrates the vibration plate 201 periodically according to the rotation cycle.

Next, descriptions are given below of placement of components around the vibration plate 201 in the sub-hopper 200 and the structure for the agitator 205 to flip the vibration plate 201.

Figure 12:
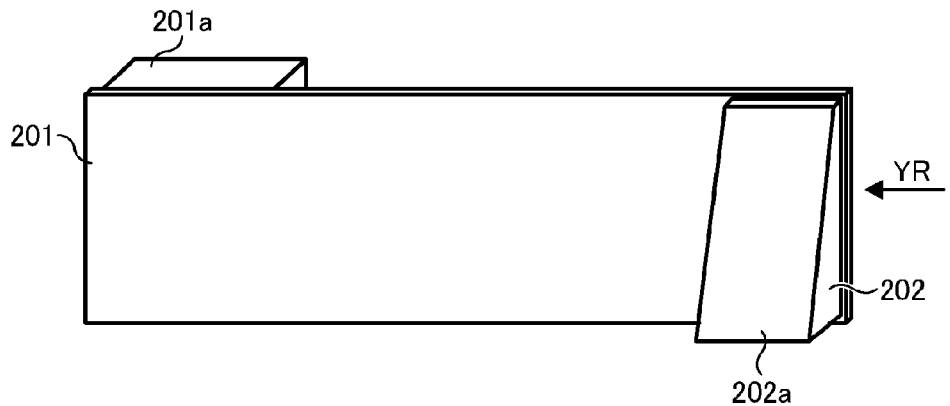
FIG. 12 is a perspective view illustrating placement of the vibration plate and adjacent components according to an embodiment.

FIG. 12 is a perspective view illustrating a component layout around the vibration plate 201. As illustrated in FIG. 12, the vibration plate 201 is secured via a mount 201a to the housing 200a of the sub-hopper 200 (in FIG. 3). In FIG. 12, reference character 202a represents an inclined face of the projection 202.

Figure 13:
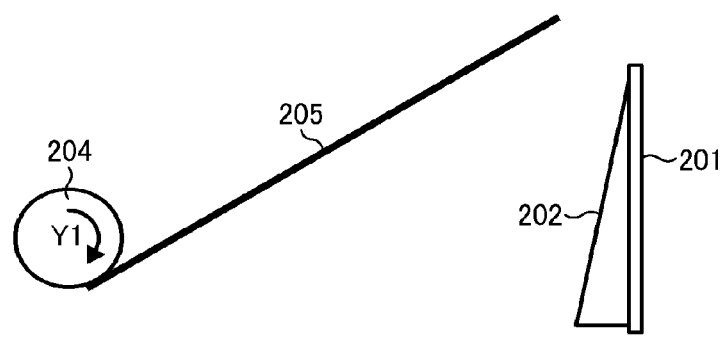
FIG. 13 is a side view illustrating relative positions of the vibration plate and an agitator according to an embodiment.

FIG. 13 is a side view illustrating a rotation position of the shaft 204. When the shaft 204 is at the position illustrated in FIG. 13, the agitator 205 is about to contact the projection 202 attached to the vibration plate 201. The shaft 204 rotates so that the agitator 205 rotates clockwise in FIG. 13 as indicated by arrow Y1.

As illustrated in FIG. 13, the projection 202 projects from a plate face (on the front side of paper on which FIG. 13 is drawn), not an end face, of the vibration plate 201 and inclined relative to the plate face of the vibration plate 201 when viewed in the direction indicated by arrow YR in FIG. 12. Specifically, the projection 202 has the inclined face 202a that approaches the shaft 204 along the direction of rotation of the agitator 205. The inclined face 202a of the projection 202 is pushed by the agitator 205 when the agitator 205 flips the vibration plate 201 to vibrate the vibration plate 201.

Figure 14:
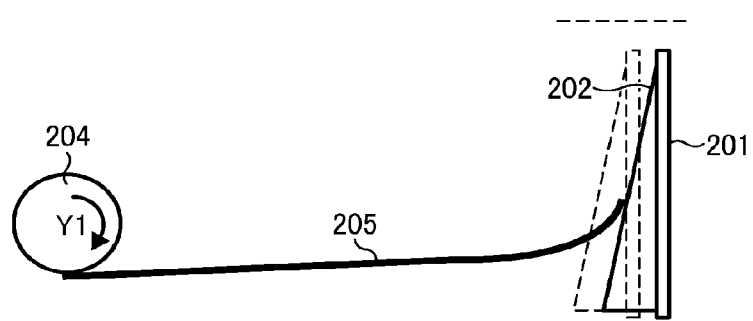
FIG. 14 is another side view illustrating the relative positions of the vibration plate and the agitator.

FIG. 14 is a side view of the agitator 205, in which the agitator 205 is positioned downstream in the direction indicated by arrow Y1 from the position illustrated in FIG. 13.

As the agitator 205 rotates further while keeping in contact with the projection 202, the vibration plate 201 is pushed and deformed along the inclined face 202a of the projection 202. In FIG. 14, broken lines represent positions of the vibration plate 201 and the projection 202 in a state in which no external force is applied thereto (herein after "stationary state"). As illustrated in FIG. 14, the vibration plate 201 and the projection 202 are pushed in by the agitator 205.

Figure 15:
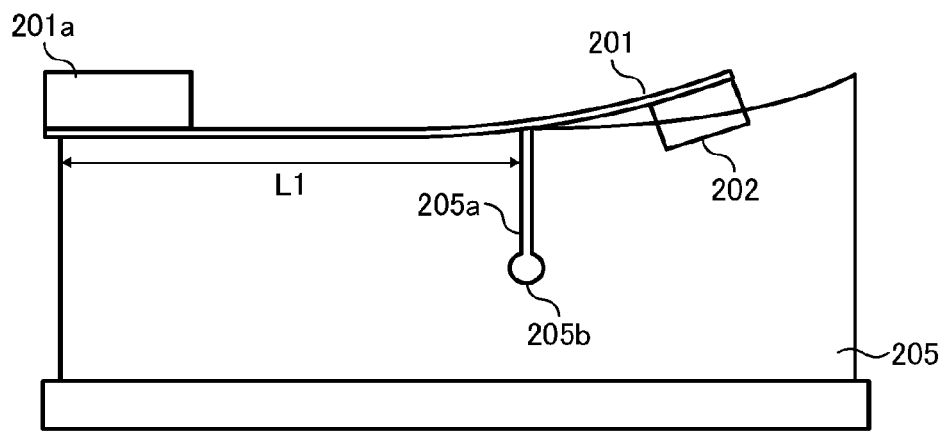
FIG. 15 is a top view illustrating the relative positions of the vibration plate and the agitator.

FIG. 15 is a top view of vibration plate 201 and the agitator 205 in the state illustrated in FIG. 14.

Since the vibration plate 201 is secured via the mount 201a to the housing 200a, the position of the first end of the vibration plate 201 on the side of the mount 201a does not change. By contrast, the opposite end of the vibration plate 201, in which the projection 202 is disposed, is pushed by the agitator 205 and moves to the side opposite the side on which the shaft 204 is positioned. Consequently, the vibration plate 201 deforms, starting from the mount 201a, as illustrated in FIG. 15. Energy to vibrate the vibration plate 201 is accumulated in the vibration plate 201 being in the deformed state.

It is to be noted that, in the configuration illustrated in FIG. 15, the agitator 205 includes a slit 205a positioned between a portion to contact the projection 202 (having a length L1 in FIG. 15) and the rest of the agitator 205. With this configuration, even if the agitator 205 receives strong force while pushing the projection 202, damage to the agitator 205 is inhibited.

The slit 205a includes a round end 205b at a start point of slit. When the amount of deformation differs between the portions adjoining via the slit 205a, the round end 205b disperses the stress given to the start point of the slit 205a, thereby inhibiting damage to the agitator 205.

Figure 16:
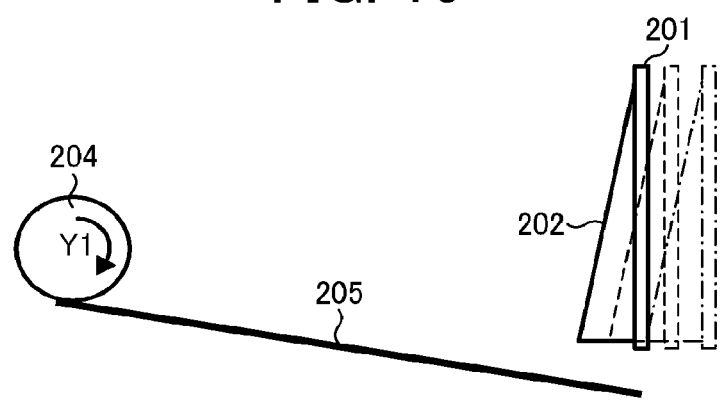
FIG. 16 is another side view illustrating the relative positions of the vibration plate and the agitator.

FIG. 16 is a side view of the agitator 205, in which the agitator 205 is positioned further downstream in the direction indicated by arrow Y1 from the position illustrated in FIG. 14.

In FIG. 16, broken lines represents the position of the vibration plate 201 being in the stationary state, and alternate long and short dashed lines represent the position of the vibration plate 201 illustrated in FIG. 14. When the vibration energy, which has been accumulated by the agitator 205 pushing the vibration plate 201, is released, the vibration plate 201 deforms to the opposite side as represented by solid lines in FIG. 16.

Figure 17:
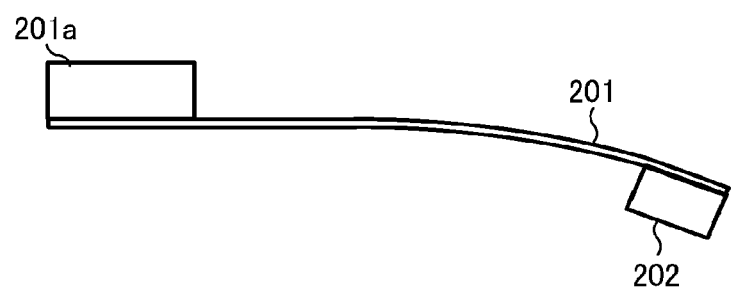
FIG. 17 is a top view illustrating vibration of the vibration plate.

FIG. 17 is a top view of vibration plate 201 in the state illustrated in FIG. 16.

As illustrated in FIG. 16, when the pushing force given to the projection 202 by the agitator 205 is released, owing to the energy of deformation accumulated in the vibration plate 201, the free end of the vibration plate 201, provided with the projection 202, deforms and moves to the opposite side.

In the state illustrated in FIGS. 16 and 17, the vibration plate 201 is away from the magnetic flux sensor 10, which faces the vibration plate 201 via the housing 200a of the sub-hopper 200. Subsequently, while the vibration plate 201 repeatedly approaches, by vibration, the magnetic flux sensor 10 further from the stationary state and moves, by vibration, away therefrom further from the stationary state, the vibration plate 201 returns to the stationary state as the vibration attenuates.

Figure 18:
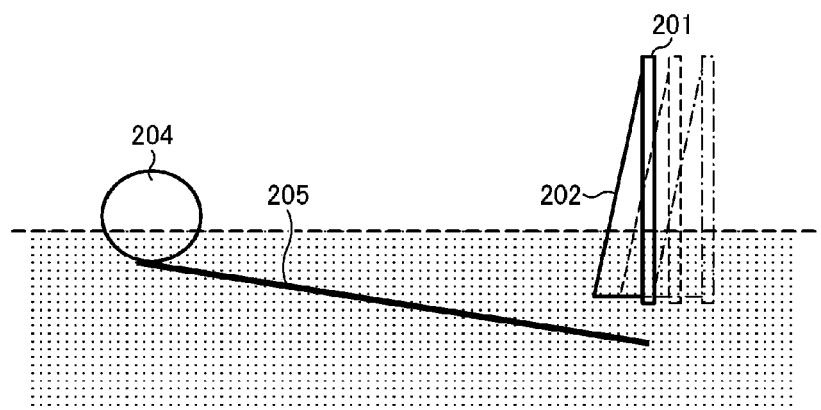
FIG. 18 is a side view illustrating the relation between the vibration of the vibration plate and developer, according to an embodiment.

FIG. 18 schematically illustrates a state of toner (represented by dots) stored in the sub-hopper 200.

When toner is present in the sub-hopper 200 as illustrated in FIG. 18, the vibration plate 201 and the projection 202 contact the toner while vibrating. Accordingly, compared with a state in which toner is not present in the sub-hopper 200, the vibration of the vibration plate 201 attenuates early. According to changes in attenuation of vibration, the amount of remaining toner in the sub-hopper 200 is detected.

Figure 19:
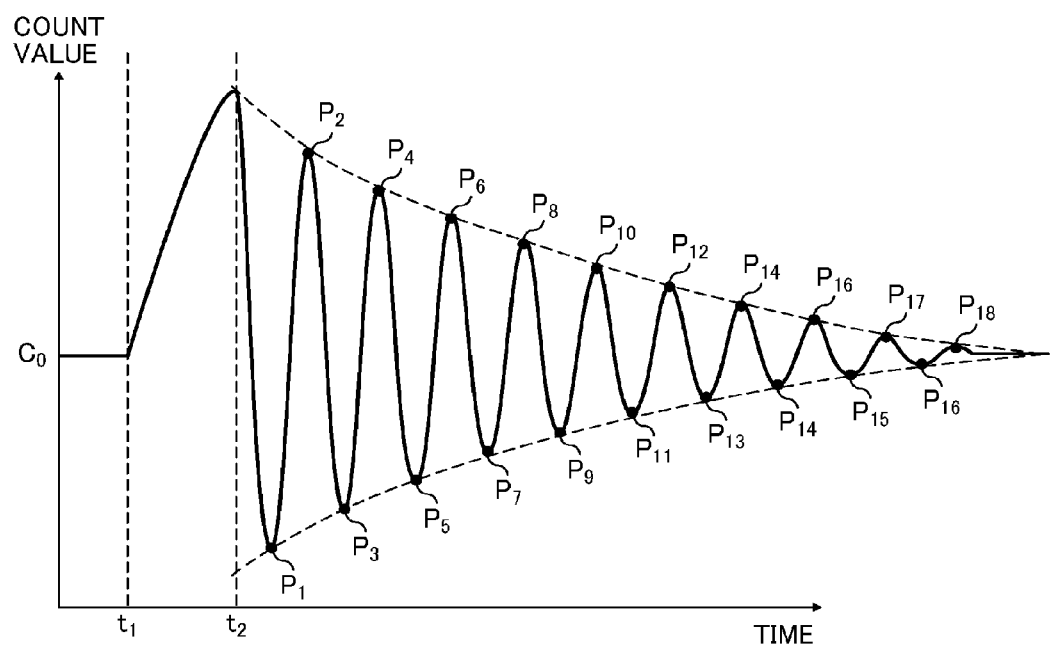
FIG. 19 is a graph of changes over time in oscillation frequency of the magnetic flux sensor corresponding to attenuation of vibration of the vibration plate.

FIG. 19 is a graph of changes in the count value of the oscillation signal from the magnetic flux sensor 10 per counting period from when the agitator 205 flips the projection 202 until the vibration of the vibration plate 201 attenuates to cease. Reference $C_0$ represents the count value at a neutral state.

The count value of the oscillation signal increases as the oscillation frequency becomes higher. Accordingly, as the ordinate in FIG. 19, the count value is replaceable with the oscillation frequency.

As illustrated in FIG. 19, at Time point $t_1$, the agitator 205 contacts and pushes the projection 202, and the vibration plate 201 approaches the magnetic flux sensor 10. Then, the oscillation frequency of the magnetic flux sensor 10 increases, and the count value per counting period increases.

At Time point $t_2$, the pushing of the projection 202 by the agitator 205 is released. Subsequently, the vibration plate 201 vibrates owing to the accumulated vibration energy. As the vibration plate 201 vibrates, the distance between the magnetic flux sensor 10 repeatedly increases and decreases from that distance in the stationary state. Consequently, the frequency of the oscillation signal of the vibration plate 201 fluctuates inherent to the vibration of the vibration plate 201, and the count value per counting period fluctuates similarly.

The amplitude of vibration of the vibration plate 201 becomes narrower as the vibration energy is consumed. That is, the vibration of the vibration plate 201 attenuates with elapse of time. Accordingly, the change in distance between the vibration plate 201 and the magnetic flux sensor 10 decreases with elapse of time. Similarly, the change in count value changes with elapse of time.

As described above, the vibration of the vibration plate 201 attenuates earlier when the amount of toner remaining in the sub-hopper 200 is greater. Accordingly, how the vibration of the vibration plate 201 attenuates is recognizable by analyzing the manner of attenuation of the oscillation of the signal output from the magnetic flux sensor 10 illustrated in FIG. 19. Then, the amount of toner remaining in the sub-hopper 200 is recognizable.

Referring to FIG. 19, when $P_1, P_2, P_3, P_4 \ldots$ represent the peaks of the count values of the oscillation signal, respectively, an attenuation ratio $\zeta$ of the vibration of the vibration plate 201 can be obtained by, for example, Formula 2 below. By referring to the change ratio between one peak value and another peak value acquired at different time points as expressed by Formula 2, errors caused by environmental changes are canceled, thereby attaining more accurate attenuation ratio. Specifically, in Formula 2, the ratio between the difference between Peaks $P_1$ and $P_2$, and the difference between Peaks $P_5$ and $P_6$ is calculated. In other words, the CPU 21 according to the present embodiment obtains the attenuation ratio based on the ratio of the count values acquired at different time points.

$$\zeta = \frac{P_6 - P_5}{P_2 - P_1} \qquad \text{Formula 2}$$

It is to be noted that, although Formula 2 above uses Peaks $P_1$ and $P_2$, and Peaks $P_5$ and $P_6$ out of the peaks illustrated in FIG. 19, this is an example, and other peaks may be used instead. However, it is preferred to exclude the peak at Time point $t_2$, at which the vibration plate 201 pushed by the agitator 205 is closest to the magnetic flux sensor 10 since this peak includes error. For example, the friction between the agitator 205 and the projection 202 causes a sliding noise, which is superimposed on the peak.

Even if the toner in the sub-hopper 200 accelerates the attenuation of the vibration, as illustrated in FIG. 18, the vibration frequency of the vibration plate 201 does not change significantly. Accordingly, by calculating the ratio between the amplitude of specific peaks as expressed in Formula 2, the attenuation of amplitude in the specific period can be calculated.

Next, descriptions are given below of detection of amount of toner remaining in the sub-hopper 200 according to the present embodiment with reference to FIG. 20.

Figures 20, 21:
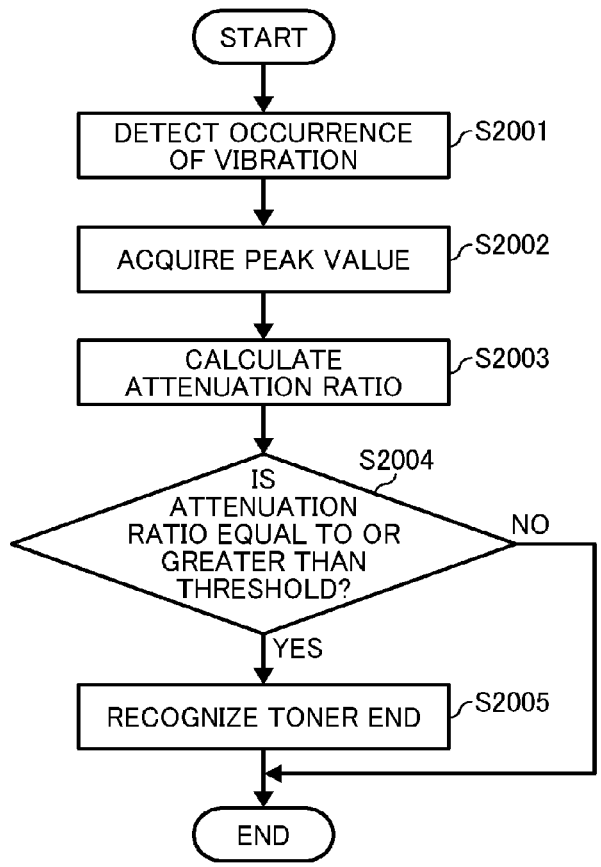
FIG. 20 is a flowchart of detection of toner remaining amount according to an embodiment.
FIG. 21 is a table of data in count value analysis according to an embodiment.

FIG. 20 illustrates a flow of actions of the CPU 21 illustrated in FIG. 8. As illustrated in FIG. 20, at S2001, the CPU 21 detects the occurrence of vibration as the agitator 205 pushes the projection 202 as illustrated in FIG. 14.

As described above, the CPU 21 acquires, from the count value output 33, the count value of the signal output from the magnetic flux sensor 10 per counting period. In the stationary state, the count value $C_0$ illustrated in FIG. 19 is obtained. By contrast, as the projection 202 is pushed as illustrated in FIG. 14 and the vibration plate 201 approaches the magnetic flux sensor 10 accordingly, the count value increases. Accordingly, at S2001, the CPU 21 detects the occurrence of vibration when the count value acquired from the count value output 33 exceeds the threshold.

Regardless of step S2001, the CPU 21 keeps acquiring the count value per counting period. At S2002, the CPU 21 acquires the peak value of fluctuation of the count value, which accords with the vibration of the vibration plate 201 illustrated in FIG. 19. The CPU 21 continuously analyzes the count value acquired in each counting period, thereby identifying the peak.

FIG. 21 is a table of data of count analysis.

The data in FIG. 21 include "number n", "count value $S_n$" acquired in each counting period, and the sign (+ or −) of the difference $(S_{n-1}-S_n)$ between each count value $S_n$ and the immediately preceding count value $S_{n-1}$. The "number n", "count value $S_n$", and the sign (+ or −) are arranged in the order of acquisition. In the data illustrated in FIG. 21, the peak is immediately before the sing of "$S_{n-1}-S_n$" is inverted. In the case illustrated in FIG. 21, "5" and "10" in the number n are adopted as peaks.

That is, subsequent to S2001, the CPU 21 calculates "$S_{n-1}-S_n$" regarding the count values sequentially acquired. The count value Sn of the number n immediately before the sign of "$S_{n-1}-S_n$" is inverted is adopted as $P_1, P_2, P_3 \ldots$ illustrated in FIG. 19.

As described above, it is preferred to avoid the count value at Timing $t_2$, which is an initial peak after the step S2001. Accordingly, the CPU 21 discards the initial peak out of the extracted peaks through the analysis illustrated in FIG. 22.

Figure 22:
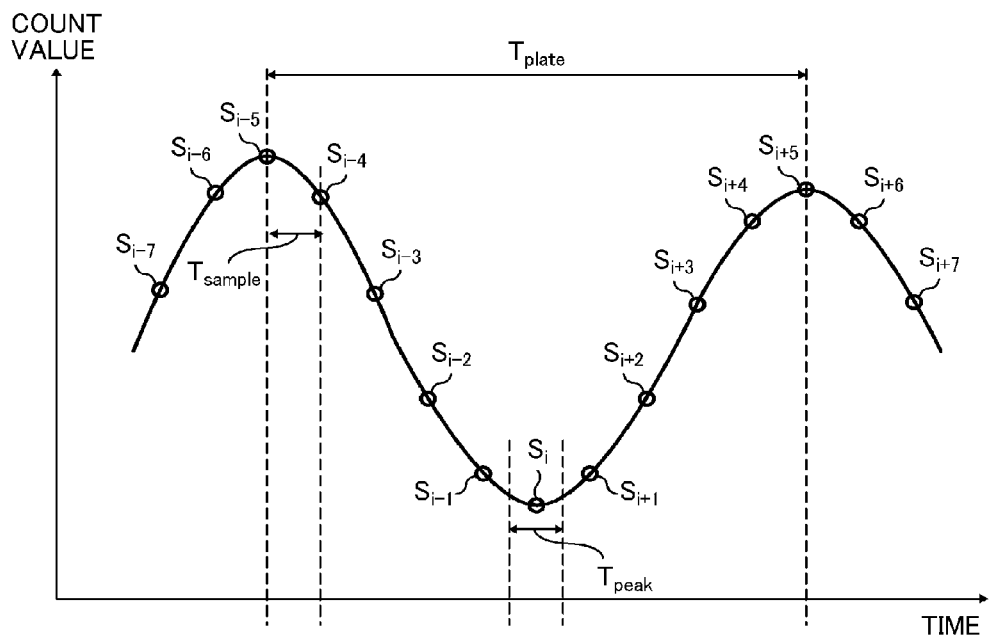
FIG. 22 is a chart illustrating the relation between a count value sampling cycle and a vibration cycle of the vibration plate according to an embodiment.

Additionally, in practice, it is possible that the count value include noise of high frequency component, and the sign of "$S_{n-1}-S_n$" may be inverted at a timing different from the timing at which the vibration of the vibration plate 201 is at its peak. To avoid erroneous detection in such cases, it is preferred that the CPU 21 smooth the values acquired from the count value output 33 before analyzing the values as illustrated in FIG. 22. The acquired values can be smoothed through typical methods such as moving average.

Using the peaks thus obtained, at S2003, the CPU 21 calculates the attenuation ratio $\zeta$ using Formula 2 mentioned above. For that, the count value analysis illustrated in FIG. 21 is continued at S2002 until the peaks used in the attenuation ratio calculation are attained. In the case of Formula 2, the CPU 21 analyzes the count values until the peak value equivalent to Peak $P_6$ is attained.

At S2004, the CPU 21 determines whether the attenuation ratio $\zeta$ calculated at S2003 is equal to or smaller than the threshold. In other words, the CPU 21 determines whether the amount of toner in the sub-hopper 200 is below the predetermined amount based on the comparison between the difference of the count values acquired at different time points and the threshold. As described above with reference to FIG. 18, when a sufficient amount of toner is in the sub-hopper 200, the vibration of the vibration plate 201 attenuates early, and the attenuation ratio $\zeta$ is smaller.

By contrast, as the amount of toner in the sub-hopper 200 decreases, the speed of attenuation of the vibration of the vibration plate 201 becomes slower, and the attenuation ratio $\zeta$ increases. Accordingly, when the threshold is set to the attenuation ratio $\zeta_s$ corresponding to the amount of remaining toner to be detected, whether the amount of toner remaining in the sub-hopper 200 falls to the amount to be detected (hereinafter "prescribed amount") can be determined based on the calculated attenuation ratio $\zeta$.

It is to be noted that the amount of toner remaining in the sub-hopper 200 does not directly affect the manner of attenuation of vibration of the vibration plate 201. According to the amount of remaining toner, the manner of contact of toner with the vibration plate 201 changes, and the manner of contact defines the manner of attenuation of vibration of the vibration plate 201. Therefore, even if the amount of toner remaining in the sub-hopper 200 is the same, the vibration of the vibration plate 201 attenuates differently depending on the manner of contact between the vibration plate 201 and toner.

In the present embodiment, the agitator 205 constantly stirs the toner in the sub-hopper 200, the amount of which is to be detected. Accordingly, to a certain degree, the state of contact of toner with the vibration plate 201 is determined with the amount of remaining toner. This configuration can avoid the inconvenience that the detection result differs depending on the manner of contact between the vibration plate 201 and toner even if the remaining amount is the same.

When the CPU 21 determines that the calculated attenuation ratio ζ is below the threshold (No at S2004), the CPU 21 determines that the amount of toner in the sub-hopper 200 is sufficient and completes the processing. By contrast, when the calculated attenuation ratio is equal to or greater than the threshold (Yes at S2004), the CPU 21 determines that the amount of toner in the sub-hopper 200 is below the prescribed amount and, at S2005, recognizes the toner end in the sub-hopper 200. Then, the processing is completed.

Recognizing the toner end at S2005, the CPU 21 outputs a signal indicating that the amount of remaining toner is below the prescribed amount, to an upper level controller to control the image forming apparatus 100. With this signal, the controller of the image forming apparatus 100 recognizes the end of toner of specific color and becomes capable of supplying toner from the toner bottle 117.

Next, descriptions are given below of the relation among the oscillation frequency of the magnetic flux sensor 10, the cycle in which the CPU 21 acquires the count values (hereinafter "sampling cycle"), and the eigenfrequency of the vibration plate 201.

FIG. 22 is a chart of count values sampled regarding a single vibration cycle of the vibration plate 201. In FIG. 22, the vibration cycle of the vibration plate 201 is represented by "$T_{plate}$", and the sampling cycle is represented by "$T_{sample}$".

To calculate, at a higher degree, the attenuation ratio ζ of the vibration of the vibration plate 201 through the method illustrated in FIGS. 19 through 21, it is necessary to acquire the peak value of vibration of the vibration plate 201 accurately. For that, it is preferred that the number of sampled count values in the vibration cycle $T_{plate}$ be sufficient, and the sampling cycle $T_{sample}$ be small enough relative to the vibration cycle $T_{plate}$.

In the case illustrated in FIG. 22, the count values $S_{i-5}$ to $S_{i+5}$ are sampled in one vibration cycle $T_{plate}$, and the number of count values ($S_i$) sampled is 10. That is, the sampling cycle $T_{sample}$ is 1/10 of the vibration cycle $T_{plate}$. In the case illustrated in FIG. 22, the count value $S_i$ is inevitably sampled during a peak period $T_{peak}$ of the count value, and thus the peak value can be acquired with a higher degree of accuracy.

Accordingly, for example, when the sampling cycle $T_{sample}$ for the CPU 21 to acquire the count values is 1 ms, the vibration cycle $T_{plate}$ of the vibration plate 201 is preferably 10 ms or greater. In other words, regarding a sampling frequency 1000 Hz of the CPU 21, the eigenfrequency of the vibration plate 201 is preferably about 100 Hz and, more preferably, not greater than 100 Hz. Such an eigenfrequency of the vibration plate 201 is attained by adjusting the material of the vibration plate 201, the dimension (including thickness) of the vibration plate 201, and the weight of the projection 202.

By contrast, if the count value acquired per each sampling cycle is too small, changes in the sampled count values corresponding to the vibration of the vibration plate 201 are small, and it becomes difficult to accurately calculate the attenuation ratio ζ. Here, the count value sampled conforms to the oscillation frequency of the magnetic flux sensor 10.

Typically, the oscillation frequency of the magnetic flux sensor 10 is of the order of several megahertz (MHz). When the sampling is performed at a sampling frequency of 1000 Hz, 1000 count values or greater are obtained at each sampling timing. According to the order of the vibration cycle $T_{plate}$ and the sampling cycle $T_{sample}$, the attenuation ratio ζ can be calculated accurately.

However, the amplitude of fluctuation of the count values relative to time illustrated in FIG. 19 is small if the change in the oscillation frequency of the magnetic flux sensor 10 is insufficient relative to the change in distance between the magnetic flux sensor 10 and the vibration plate 201. The change in distance therebetween is defined by the vibration of the vibration plate 201. As a result, the change in the attenuation ratio ζ also becomes smaller, thereby degrading the accuracy in detecting the amount of remaining toner, using the vibration of the vibration plate 201.

To increase the change in oscillation frequency of the magnetic flux sensor 10 corresponding to the change in distance between the magnetic flux sensor 10 and the vibration plate 201, the distance therebetween is determined based on the characteristics illustrated in FIG. 11. For example, it is preferred that the distance between the magnetic flux sensor 10 and the vibration plate 201 (in the stationary state) be set to the distance that corresponds to the range in which the oscillation frequency changes steeply corresponding to the distance therebetween, such as the range FL in FIG. 11.

Figure 23:
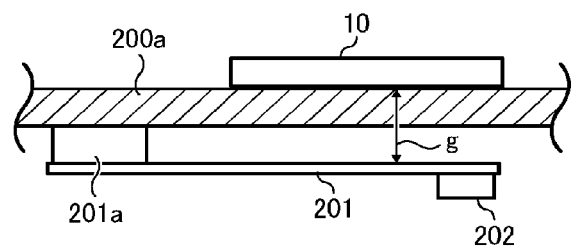
FIG. 23 illustrates a distance of the magnetic flux sensor and the vibration plate according to an embodiment.

FIG. 23 is a view illustrating adjustment of the distance between the magnetic flux sensor 10 and the vibration plate 201.

As illustrated in FIG. 23, a distance g between the magnetic flux sensor 10 and the vibration plate 201 in the stationary state is adjustable with the thickness of the housing 200*a* of the sub-hopper 200, to which the magnetic flux sensor 10 and the vibration plate 201 are secured, and the thickness of the mount 201*a*, to which the vibration plate 201 is mounted.

In the above-described method according to the present embodiment, the effect of toner on the vibration of the vibration plate 201, which is a delicate phenomenon, is detected to detect the amount of remaining toner. This method is advantageous over a method in which the pressure of toner or the like is directly detected. Since the state of toner is detected via the vibration of the vibration plate 201, this method enables accurate detection of toner remaining amount without using a pressure sensor, the accuracy of which is not easily enhanced.

Additionally, the present embodiment is on the premise that the vibration plate 201 being sensed by the magnetic flux sensor 10 is vibrating. Therefore, even if toner is on the vibration plate 201, the toner is shaken off the vibration plate 201 as the vibration plate 201 vibrates. Thus, degradation of detection accuracy caused by toner adhesion is inhibited.

Additionally, it is not necessary that the magnetic flux sensor 10 physically contacts the vibration plate 201 being sensed. Even if the magnetic flux sensor 10 is disposed outside the toner container (sob-hopper 200 in the present embodiment), it is not necessary to make a hole in the housing to attain physical access. Thus, attachment of components is easy, thereby improving productivity.

Additionally, according to the present embodiment, as presented as S2001 in FIG. 20, the detection of toner remaining amount is triggered when the vibration plate 201 moves, pushed by the agitator 205, and the toner remaining amount is detected by acquiring the subsequent peak values. Accordingly, detection results of toner remaining amount are not attained in the state illustrated in FIG. 14, in which the vibration plate 201 is pushed by the agitator 205.

By contrast, in the method that employs a pressure sensor or the like to detect pressure corresponding to the toner remaining amount, it is difficult to distinguish the pressure caused by the agitator 205 stirring the toner inside the toner container from the pressure corresponding to the toner remaining amount. Thus, it is difficult to improve the detection accuracy. Such inconveniences are eliminated in the present embodiment.

It is to be noted that, although the above-described embodiment employs the vibration plate 201 that is planar and made of metal, this is just an example. Requisites of the vibration plate 201 include generating vibration at a desired vibration frequency as described with reference to FIG. 22, affecting the magnetic flux corresponding to the distance from the magnetic flux sensor 10, and affecting the frequency of oscillation signal of the magnetic flux sensor 10 accordingly.

The description above concerns use of a metal component that cancels the magnetic flux, thereby reducing the inductance L, as the metal component approaches the magnetic flux sensor 10. Alternatively, another embodiment employs a ferromagnetic component, which increases the magnetic flux, thereby increasing the inductance L, as the ferromagnetic component approaches the magnetic flux sensor 10.

In the above-described embodiment, the target sensed by the magnetic flux sensor 10 is planar (i.e., the vibration plate 201) from the standpoint of effects on magnetic flux generated by the coil pattern 11 of the magnetic flux sensor 10 and the standpoint of eigenfrequency. However, the target sensed by the magnetic flux sensor 10 is not limited to the planar component but can be, for example, a rod as long as the rod vibrates and affects the magnetic flux.

Additionally, in the description above, the vibration plate 201 is made of a material that affects the magnetic flux, and the attenuation of vibration of the vibration plate 201 is detected by the magnetic flux sensor 10. However, this is just an example, and the material is not limited thereto as long as the toner remaining amount in the toner container is detectable based on the effects of toner on the vibration of the planar component, which is a delicate phenomenon.

Accordingly, not limited to the configuration in which the magnetic flux sensor 10 is provided and the vibration plate 201 is made of the material to affect magnetic flux, the effects similar to those described above can be attained with a function to detect the vibration of the vibration plate 201 disposed inside the toner container. For example, in another embodiment, a sensor to directly detect vibration is disposed at a position to which the vibration of the vibration plate 201 is transmitted. For example, the sensor is disposed at the mount 201a or the projection 202.

The above-described prescribed amount is adjustable with the placement of the vibration plate 201 and the magnetic flux sensor 10 in the sub-hopper 200.

Figure 24:
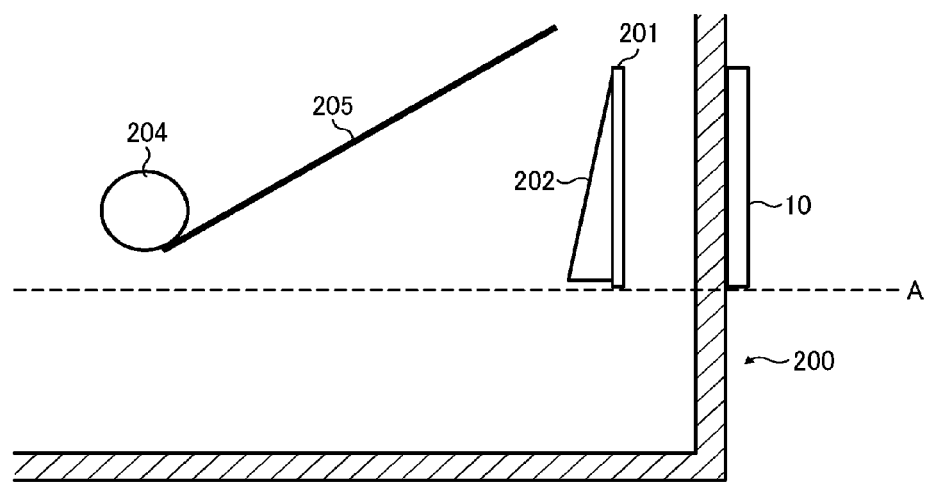
FIG. 24 is a view illustrating heights of the vibration plate and the magnetic flux sensor secured in the sub-hopper according to an embodiment.
Figure 25:
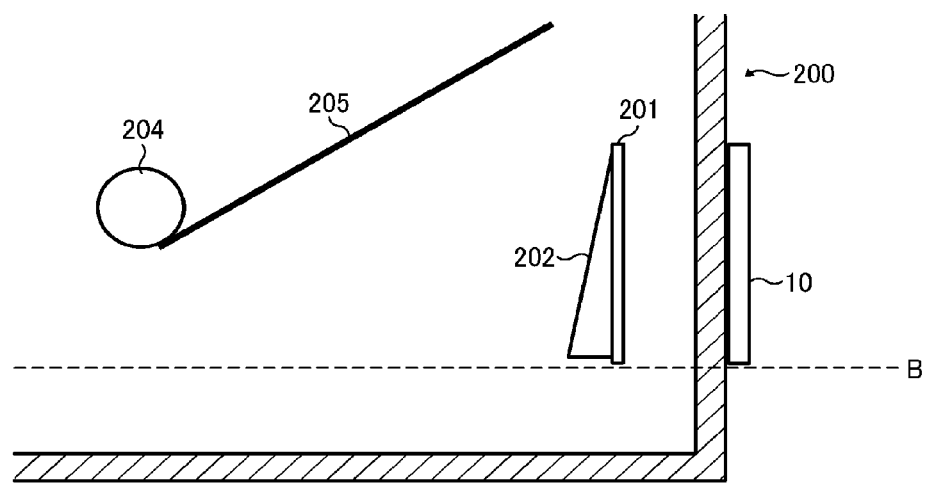
FIG. 25 is a another view illustrating heights of the vibration plate and the magnetic flux sensor secured in the sub-hopper.

FIGS. 24 and 25 are views illustrating the relation between the placement of the vibration plate 201 and the magnetic flux sensor 10 in the sub-hopper 200 and the prescribed amount.

In the case illustrated in FIG. 24, toner does not contact the vibration plate 201 when the level (height) of toner in the sub-hopper 200 falls below a height A indicated by broken lines in FIG. 24. Accordingly, when the level of toner is around the height A, the CPU 21 recognizes that the toner remaining amount falls below the prescribed amount.

By contrast, in the case illustrated in FIG. 25, the vibration plate 201 and the magnetic flux sensor 10 are at positions lower than those illustrated in FIG. 24. Toner does not contact the vibration plate 201 when the level (height) of toner in the sub-hopper 200 falls below a height B indicated by broken lines in FIG. 25. Accordingly, when the level of toner is around the height B, it is deemed that the toner remaining amount is below the prescribed amount.

For example, to adjust the manners to supply cyan, magenta, yellow, and black toners, the prescribed amount is adjusted with the placement of the vibration plate 201 and the magnetic flux sensor 10. For example, regarding a frequently used color among cyan, magenta, yellow, and black, the vibration plate 201 and the magnetic flux sensor 10 are disposed at higher positions as illustrated in FIG. 24. By contrast, regarding the color used less frequently, the vibration plate 201 and the magnetic flux sensor 10 are disposed at lower positions as illustrated in FIG. 25. With such adjustment, toner can be supplied efficiently corresponding to the frequency of use.

Additionally, although the description above concerns the detecting mechanism including the magnetic flux sensor 10 and the vibration plate 201 to detect the amount of toner remaining in the sub-hopper 200 illustrated in FIG. 2, this detecting mechanism can be widely used to detect the amount of powder such as toner. For example, the detecting mechanism is used to detect the amount of toner remaining in the developing device 112 in another embodiment.

Figure 26:
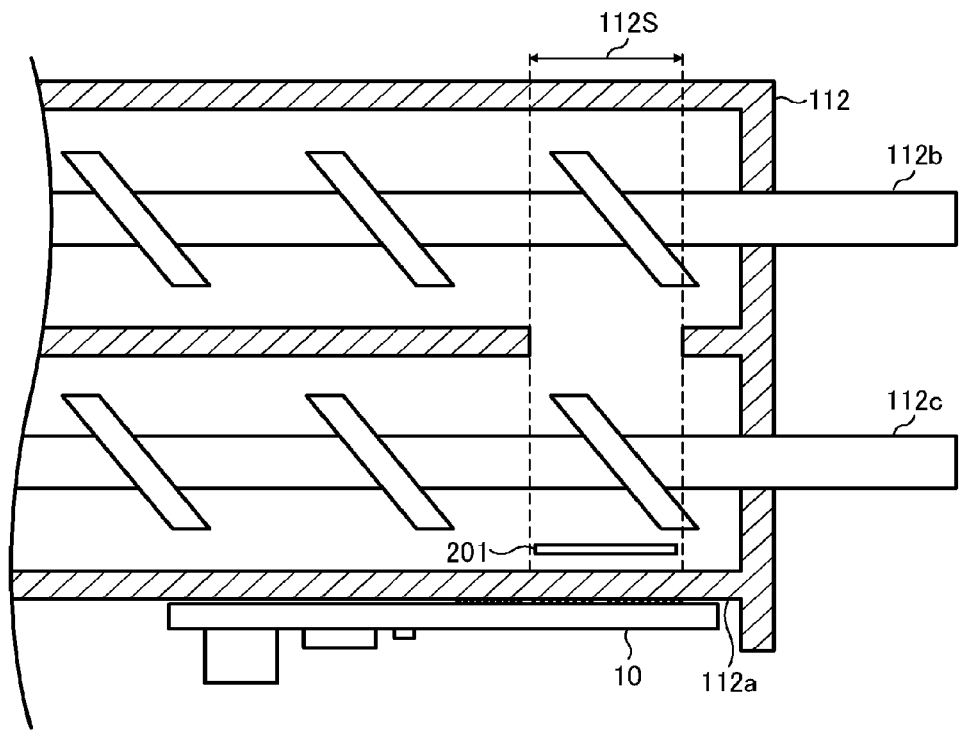
FIG. 26 is a cross-sectional view illustrating placement of the magnetic flux sensor and the vibration plate disposed in the developing device, according to an embodiment.

FIG. 26 is a cross-sectional view of the developing device 112 in that case. Inside the developing device 112, a supplying screw 112b and a collecting screw 112c transport toner by rotation.

The supplying screw 112b and the collecting screw 112c serve as developer conveyors and transport toner in the main scanning direction entirely in the developing device 112. The developer conveyors are not limited to screws but can be augers, coils, or paddles.

When the detecting mechanism including the magnetic flux sensor 10 and the vibration plate 201 is applied to the developing device 112, as illustrated in FIG. 26, the magnetic flux sensor 10 is attached to the developing device 112 such that the board face bearing the coil pattern 11 faces a sensor mounting portion 112a in the developing device 112. With this placement, as illustrated in FIG. 26, the coil pattern 11 is disposed facing a communicating space 112S through which a developer conveyance passage by the collecting screw 112c communicates with a developer conveyance passage by the supplying screw 112b.

Inside the developing device 112, the vibration plate 201 is disposed in the communicating space 112S. Similar to the vibration plate 201 disposed in the sub-hopper 200, the vibration plate 201 disposed in the developing device 112 vibrates, flipped by the collecting screw 112c that rotates. With this action, similar to the above-described embodiment, the magnetic flux sensor 10 can detect the vibration of the vibration plate 201.

Since toner moves between the developer conveyance passage by the collecting screw 112c and the developer conveyance passage by the supplying screw 112b, the toner remains longer in the communicating space 112S than those conveyance passages, and the toner is denser in the communicating space 112S. Accordingly, the effects of toner on the vibration of the vibration plate 201 are increased by disposing the vibration plate 201 in the communicating space 112S, and thus the amount of toner remaining in the developing device 112 can be detected with a higher degree of accuracy.

Additionally, although the description above concerns detection of amount of toner (i.e., developer) used in electrophotographic image forming apparatuses, the target of remaining amount detection is not limited thereto. The aspects of this specification can adapt to detection of any powder as long as the powder affect the vibration of the vibration plate 201 has flowability to affect the vibration of the vibration plate 201 corresponding to the remaining amount. For example, the target of remaining amount detection can be premixed developer, in which toner is premixed with carrier. Further, the target of remaining amount detection is not limited to powder but can be any substance having flowability to affect the vibration of the vibration plate 201 corresponding to the remaining amount. For example, the target of remaining amount detection can be liquid.

Further, although the attenuation ratio ζ is calculated using Formula 2 in the embodiment described above, this is an example. Alternatively, for example, as expressed by Formula 3 below, an average of attenuation ratios between multiple peaks can be used.

$$\zeta = \frac{1}{2}\left(\frac{P_4 - P_3}{P_2 - P_1} + \frac{P_8 - P_7}{P_6 - P_5}\right) \quad \text{Formula 3}$$

Yet alternatively, as expressed by Formula 4 below, simply the ratio between the multiple peaks can be used.

$$\zeta = \frac{P_6}{P_2} \quad \text{Formula 4}$$

In the embodiment described above, a planar pattern coil printed on the board is used. The planar coil (i.e., in a planar pattern of wire) is advantageous in reducing the size (thickness) in the direction in which the coil faces the vibration plate 201 to be sensed, thereby making the apparatus compact.

However, similar effects are available with a coil configured to generate a magnetic flux in the direction in which the coil faces the vibration plate 201 even if the coil is not shaped in a planar pattern.

Figure 27:
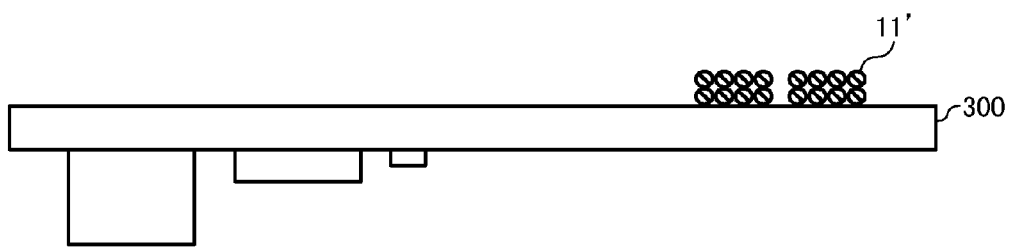
FIG. 27 is a side view illustrating a shape of a coil according to another embodiment.
Figure 28:
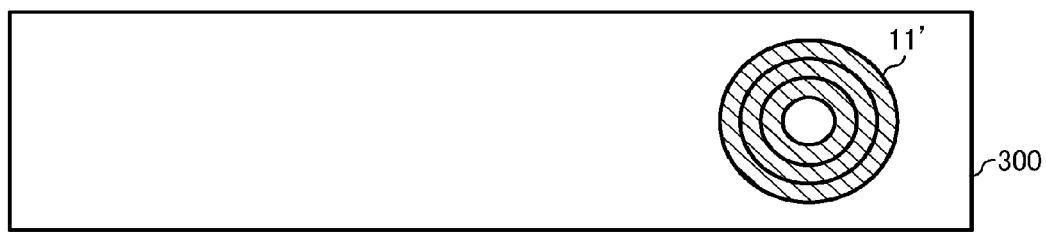
FIG. 28 is a front view of the coil illustrated in FIG. 27.

FIGS. 27 and 28 illustrate another configuration of the coil. FIG. 27 is a side view of a coil 11' as viewed in a direction parallel to the board face of the board 300. FIG. 28 is a view of the coil 11' as viewed in a direction perpendicular to the board face of the board 300.

The configuration illustrated in FIGS. 27 and 28 includes the coil 11' produced by winding wire on the board 300 serving as the magnetic flux sensor 10. A surface of the coil 11' is insulated. In the configuration illustrated in FIGS. 27 and 28, also, the coil 11' can be thin in the direction in which the coil 11' faces the vibration plate 201, thereby making the device or the apparatus compact.

Figure 29:
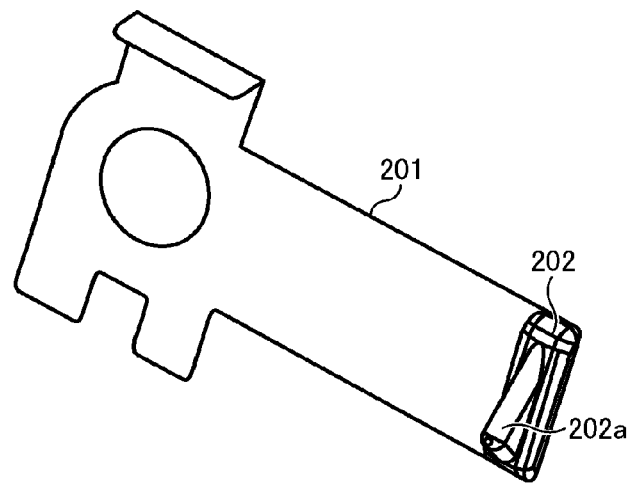
FIG. 29 illustrates the vibration plate of the sub-hopper illustrated in FIG. 4.

FIG. 29 is a perspective view of the vibration plate 201 described above with reference to FIG. 4.

In the configuration illustrated in FIGS. 4 and 29, the projection 202 is disposed on the second end (free end) of the vibration plate 201, which is opposite the first end secured to the mount 201a. In this configuration, the projection 202 defines the inclined face 202a, with which the agitator 205 flips the vibration plate 201.

Although the projection 202 extends over the entire width of the vibration plate 201 in the direction in which the agitator 205 moves while being in contact with the vibration plate 201, alternatively, the projection 202 may present on a part of the vibration plate 201.

Figure 30:
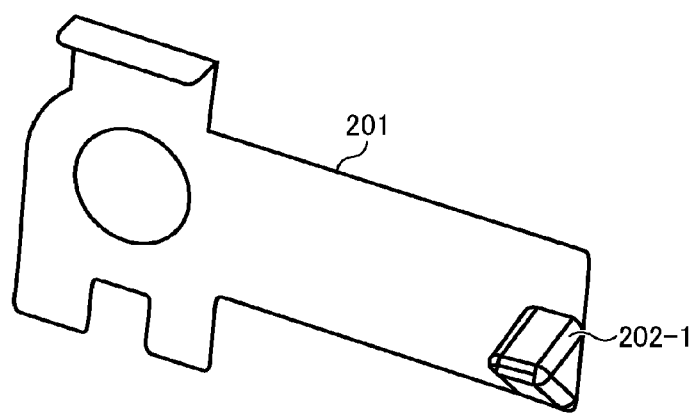
FIG. 30 is a view of a variation of the vibration plate illustrated in FIG. 29.

FIG. 30 illustrates a projection 202-1 that extends a part of the vibration plate 201 in the direction in which the agitator 205 moves on the vibration plate 201.

However, the inclination in the range in which the agitator 205 contacts the projection 202 is to be considered. If the inclination changes in the range in which the agitator 205 contacts the projection 202 as illustrated in FIG. 30, while the vibration plate 201 is being pushed as illustrated in FIG. 14, it is possible that the strength of force to push the vibration plate 201 changes, thereby affecting the vibration of the vibration plate 201 flipped. Accordingly, it is preferred that the inclination of the projection 202 be uniform in the range in which the agitator 205 contacts the projection 202.

Figure 31:
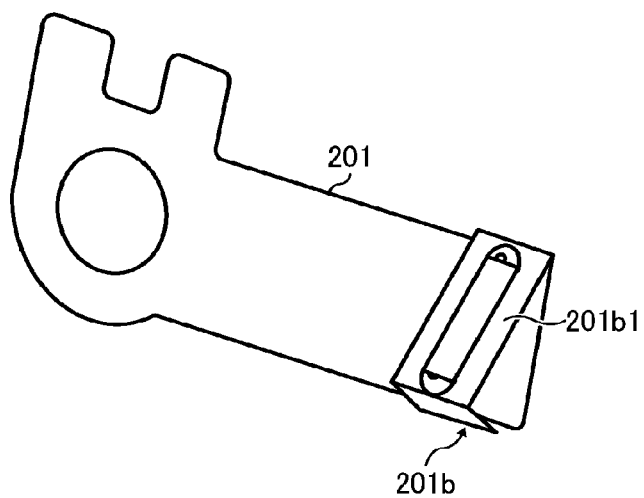
FIG. 31 is a view of another variation of the vibration plate.
Figure 32:
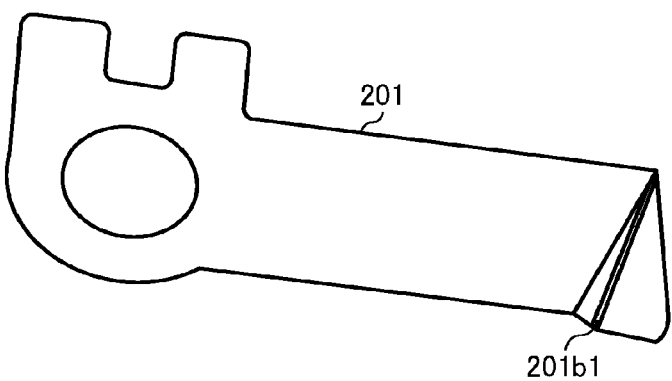
FIG. 32 is a view of yet another variation of the vibration plate.

The inclined face 202a can be attained by disposing the projection 202, which is a different component from the vibration plate 201, on the second end. Alternatively, in FIG. 31, the vibration plate 201 includes a bent metal piece 201b extending from the second end thereof, and the metal piece 201b includes an inclined portion 201b1. Yet alternatively, as illustrated in FIG. 32, the inclined portion 201b1 is produced by stereoscopically bending the second end of the vibration plate 201, without providing the metal piece 201b.

These configurations are advantageous particularly in cases where attaching a different component to the vibration plate 201 hinders the vibration plate 201 from having the preferred eigenfrequency described above.

Figure 33:
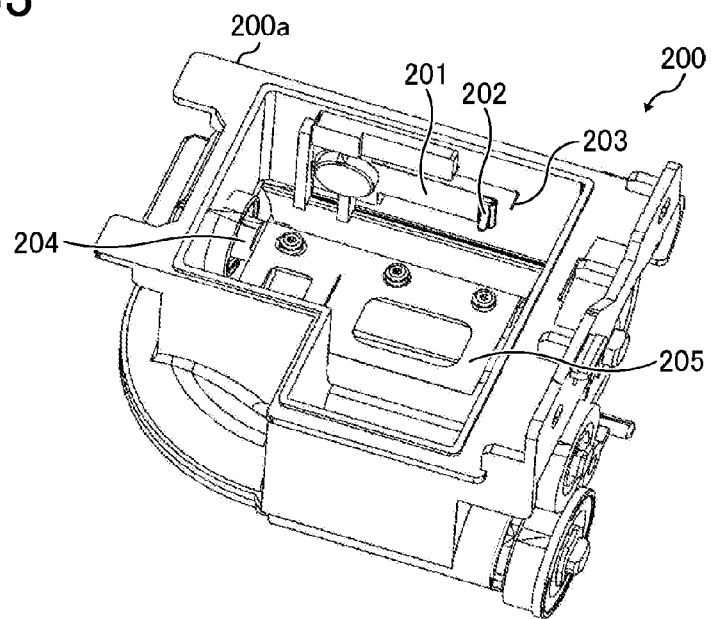
FIG. 33 is a perspective view illustrating a sub-hopper according to a variation.

FIG. 33 is a perspective view illustrating an interior of a sub-hopper according to a variation.

The configuration illustrated in FIG. 33 is different from that illustrated in FIG. 4 in that a rod 203 is disposed adjacent to the vibration plate 201. For example, the rod 203 is made of metal. The rod 203 has a capability to remove toner from a gap between the vibration plate 201 and the housing 200a of the sub-hopper 200, which is described below.

Figure 34:
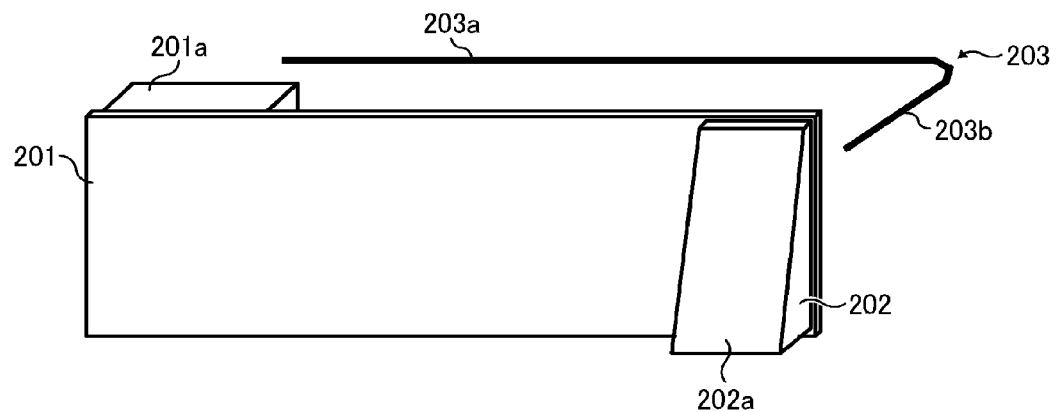
FIG. 34 is a perspective view illustrating placement of a vibration plate and a rod in the sub-hopper illustrated in FIG. 33.

FIG. 34 is a perspective view illustrating placement of the vibration plate 201 and the rod 203 in the sub-hopper 200 illustrated in FIG. 33.

As illustrated in FIG. 34, the vibration plate 201 is secured via the mount 201a to the housing 200a of the sub-hopper 200 illustrated in FIG. 33. The rod 203 includes a rod body 203a and a hook portion 203b, and an end of the rod body 203a is bent at a right angle or substantially right angle and shaped into the hook portion 203b. The rod body 203a extends parallel to the long side of the vibration plate 201, and the hook portion 203b is bent from the rod body 203a in the direction perpendicular to the plate face of the vibration plate 201.

Figure 35:
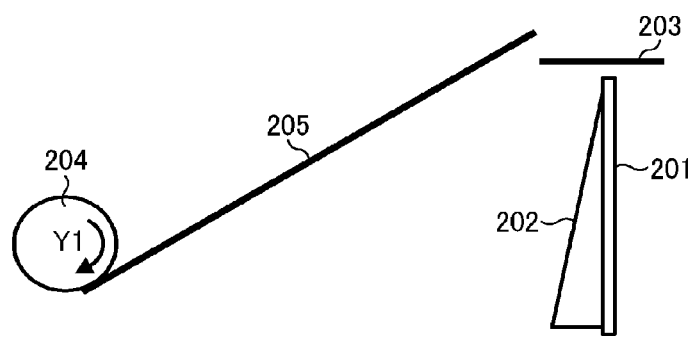
FIG. 35 is a side view illustrating the relative positions of the vibration plate and the agitator in the configuration illustrated in FIGS. 33 and 34.

FIG. 35 is a side view illustrating a rotation position of the shaft 204, at which the agitator 205 is about to contact the rod 203 and the projection 202 attached to the vibration plate 201. The shaft 204 rotates so that the agitator 205 rotates clockwise in FIG. 35.

As illustrated in the side view in FIG. 35, the projection 202 is inclined relative to the plate face of the vibration plate 201. The inclined face 202a of the projection 202 is pushed by the agitator 205 when the agitator 205 flips the vibration plate 201 to vibrate the vibration plate 201.

As illustrated in FIG. 35, while rotating and approaching the vibration plate 201, the agitator 205 contacts the hook portion 203b and pushes the rod 203 down before coming to contact with the projection 202.

Figure 36:
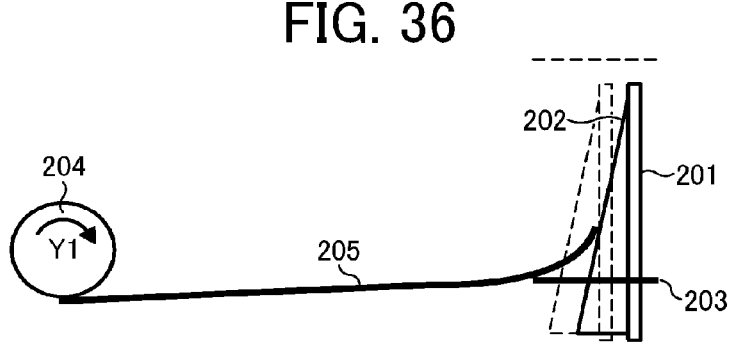
FIG. 36 is another side view illustrating the relative positions of the vibration plate and the agitator in the configuration illustrated in FIGS. 33 and 34.

FIG. 36 is a side view in which the agitator 205 is positioned downstream in the direction indicated by arrow Y1 from the position illustrated in FIG. 35. As illustrated in FIG. 36, the entire rod 203 deforms down as the hook portion 203b is pushed down by the rotating agitator 205.

Additionally, as the agitator 205 rotates further while keeping in contact with the projection 202, the vibration plate 201 is pushed along the inclined face 202a of the projection 202. In FIG. 36, broken lines represent positions of the vibration plate 201 and the projection 202 in the stationary state, in which no external force is applied thereto. As illustrated in FIG. 36, the vibration plate 201 and the projection 202 are pushed in by the agitator 205.

Figure 37:
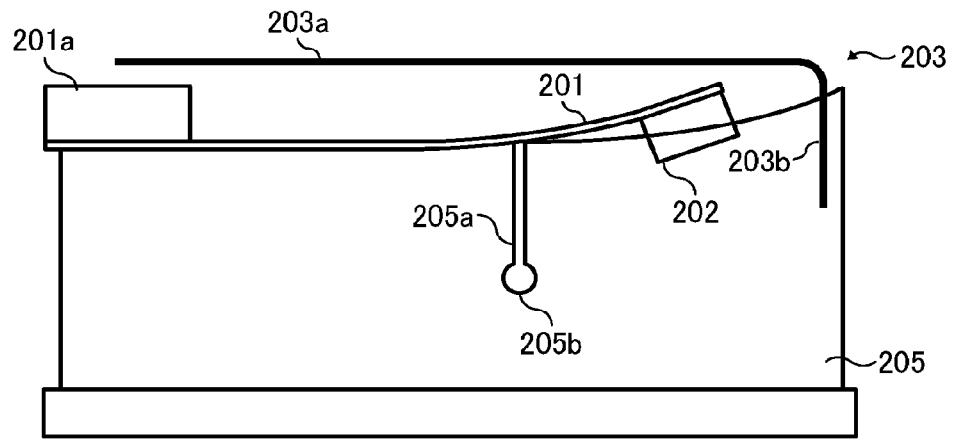
FIG. 37 is a top view of the vibration plate and the agitator in the state illustrated in FIG. 36.

FIG. 37 is a top view of the vibration plate 201 in the state illustrated in FIG. 36. Since the vibration plate 201 is secured via the mount 201a to the housing 200a (in FIG. 33), the position of the first end of the vibration plate 201 on the side of the mount 201a does not change.

By contrast, the opposite end of the vibration plate 201, in which the projection 202 is disposed, is pushed by the agitator 205 and moves to the side opposite the side on which the shaft 204 is positioned. Consequently, the vibration plate 201 deforms, starting from the mount 201a, as illustrated in FIG. 37. Energy to vibrate the vibration plate 201 is accumulated in the vibration plate 201 being in the deformed state.

Figure 38:
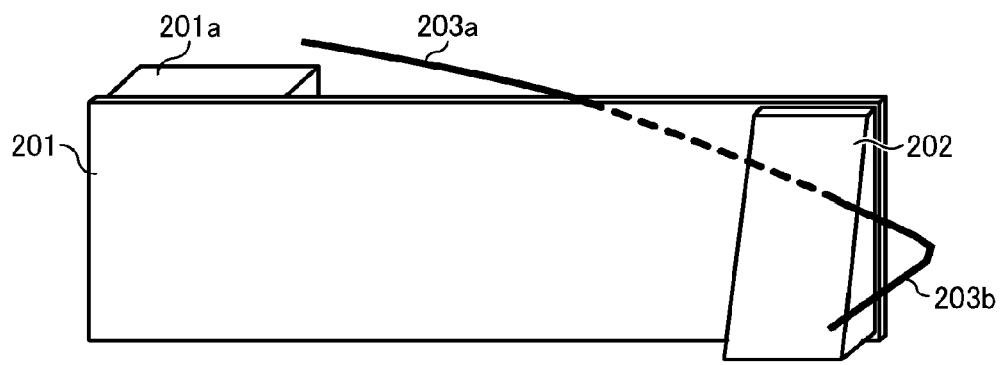
FIG. 38 is a perspective view illustrating relative positions of the vibration plate and the rod in the state illustrated in FIG. 36.

FIG. 38 is a perspective view of the rod 203 in the state illustrated in FIG. 36.

As illustrated in FIG. 38, being pushed down by the agitator 205, the rod 203 gets behind the vibration plate 201 in FIG. 38 and deforms. That is, the vibration plate 201 enters the gap between the vibration plate 201 and the inner wall of the housing 200a (illustrated in FIG. 33). Then, the rod 203 scraps off toner stuck between the vibration plate 201 and the inner wall of the housing 200a.

As described above, the vibration plate 201 gains the energy to vibrate by deforming, being pushed by the agitator 205. Therefore, if toner is stuck between the vibration plate 201 and the inner wall of the housing 200a of the sub-hopper 200, the vibration plate 201 is not sufficiently pushed in, and a sufficient energy for vibration is not accumulated.

By contrast, as illustrated in FIG. 38, the rod 203 removes toner from the gap between the vibration plate 201 and the inner wall, thereby securing a sufficient space for the vibration plate 201 to deform to accumulate the energy for vibration.

Figure 39:
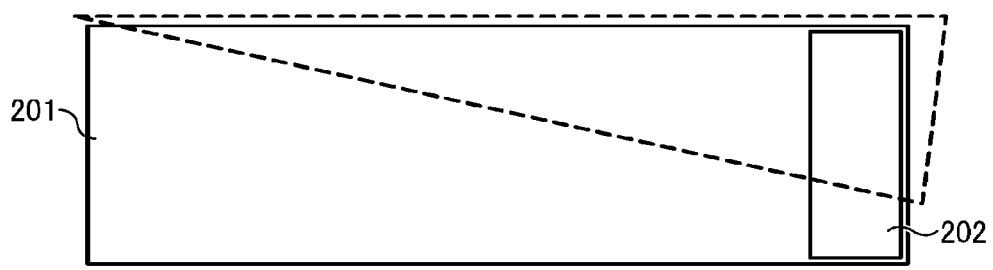
FIG. 39 illustrates s a range from which developer is removed by the rod illustrated in FIG. 38.

In FIG. 39, broken lines represent a range in which the rod 203 moves, pushed by the agitator 205. In the configuration illustrated in FIGS. 33 through 39, the rod 203 enters not an entire range occupied by the vibration plate 201 but an upper part (in FIGS. 33 and 39) of the range occupied by the vibration plate 201. With this configuration, the rod 203 can remove toner from the gap between the vibration plate 201 and the inner wall of the sub-hopper 200 to a degree sufficient for securing the space for the vibration plate 201 to deform to accumulate the energy for vibration.

Although the embodiments of the present disclosure have been described above, various aspects of the present specification can attain specific effects as follows.

Aspect A

Aspect A concerns a powder detector to detect an amount of powder in the powder container such as the sub-hopper 200 and the developing device 112. The powder, such as developer and toner, has flowability and affects a vibration state of the vibration plate. The powder detector includes a vibration plate disposed in the powder container to vibrate, a vibration detector, such as the magnetic flux sensor 10, to detect a vibration state of the vibration plate, and a contact member, such as the agitator 205, that contacts the vibration plate to vibrate the vibration plate.

Aspect B

In Aspect A, the contact member includes an agitator, such as the agitator 205 and the collecting screw 112c, to agitate the powder stored in the powder container.

Aspect C

In the powder detector according to Aspect A or B, a rotatable shaft is disposed inside the powder container, and the contact member is attached to the shaft to rotate together with the shaft. A first end of the vibration plate in an axial direction of the shaft is secured, and a second end of the vibration plate opposite the first end includes a projection (202) pressed by the contact member.

Aspect D

In the powder detector according to Aspect C, the projection includes an inclined face (such as the inclined face 202a and inclined portion 201b1) projecting toward the shaft from a face of the vibration plate, and the inclined face is inclined such as that the distance from the shaft to the inclined face decreases along the direction of rotation of the contact member.

Aspect E

In the powder detector according to Aspect D, the inclination angle of the inclined face is uniform in the range in which the contact member contacts the inclined face.

Aspect F

In the powder detector according to Aspect C or D, the projection is made of a material different from a material of the vibration plate, and the vibration plate including the projection has a predetermined vibration frequency.

Aspect G

The powder detector according to any of Aspects A through F further includes a frequency-related data output (such as the input-output control ASIC 30 including the count value output 33) to output frequency-related data, and a detection result processor, such as the CPU 21, to recognize the amount of powder in the powder container according to a detection result generated by the vibration detector such as the magnetic flux sensor 10. The vibration detector includes a signal oscillator to output a signal corresponding to the state of the magnetic flux passing through a space opposed to the vibration detector. The vibration plate is disposed facing the signal oscillator via a housing of the powder container and vibrates in a direction in which the vibration plate faces the signal oscillator. The vibration plate is made of a material, such as metal, that affects the magnetic flux. The detection result processor acquires, in each sampling cycle, frequency-related data that relates to the frequency of the oscillation signal of the signal oscillator and changes corresponding to the vibration state of the vibration plate. The detection result processor detects the vibration state of the vibration plate based on a change in the frequency-related data.

Aspect H

In the powder detector according to Aspect G, the detection result processor detects the vibration state of the vibration plate based on a change in the frequency-related data corresponding to an attenuation of vibration of the vibration plate vibrated by the contact member.

Aspect I

In the powder detector according to Aspect H, the frequency-related data includes a count value of the oscillation signal output from the signal oscillator such as the magnetic flux sensor 10, counted in each counting period, and the detection result processor detects the vibration state of the vibration plate based on a change in the count value.

Aspect J

In the powder detector according to Aspect I, regarding the count value of the oscillation signal, the detection result processor acquires a first count value and a second count value counted at different timings, and the detection result processor detects the vibration state of the vibration plate based on a ratio between the first count value and the second count value.

Aspect K

In the powder detector according to Aspect J, the detection result processor determines that the amount of powder in the powder container is blow a prescribed amount based on a comparison between a threshold and the ratio between the first count value and the second count value.

Aspect L

In the powder detector according to Aspect H, the sampling cycle in which the detection result processor acquires the frequency-related data is shorter than a vibration cycle of the vibration plate.

Aspect M

In the powder detector according to any of Aspects G through L, the signal oscillator includes a coil, such as the coil pattern 11 and the coil 11', disposed on a board to generate a magnetic flux in the direction in which the vibration plate faces the signal oscillator. The signal oscillator outputs the oscillation signal having a frequency corresponding to an inductance of the coil.

Aspect N

An image forming apparatus includes an image forming unit to form an image, the powder container such as the sub-hopper 200 and the developing device 112, and the powder detector according to any of Aspects A though M. The power container contains a powder, such as toner, carrier, and premixed developer, used by the image forming unit to form the image.

Aspect O

Aspect O concerns a powder detecting method to detect an amount of powder stored in a powder container and having flowability. The powder detecting method includes vibrating a vibration plate disposed in the powder container; detecting the vibration state of the vibration plate, with a vibration detector; and recognizing the amount of powder in the powder container according to the vibration state detected. The vibration state of the vibration plate is affected by the powder in the powder container.

Aspect P

In the powder detecting method according to Aspect O, the vibration detector includes a signal oscillator to output a signal corresponding to a state of a magnetic flux passing through a space opposed to the vibration detector. The vibration plate is disposed facing the signal oscillator via a housing of the powder container and vibrates in the direction in which the vibration plate faces the signal oscillator. The vibration plate is made of a material to affect the magnetic flux. The powder detecting method further includes outputting, from the signal oscillator, the signal corresponding to the state of the magnetic flux passing through the space opposed; acquiring, in each sampling cycle, frequency-related data that relates to the frequency of the oscillation signal of the signal oscillator and changes corresponding to the vibration state of the vibration plate; detecting the vibration state of the vibration plate based on a change in the frequency-related data, and recognizing the amount of powder in the powder container according to the vibration state detected.

Aspect Q

In any of Aspects A through P, the vibration plate is disposed facing the housing of the powder container, and the powder detector further includes a powder remover, such as the rod 203, that deforms when pushed by the contact member, thereby removing powder from a gap between the vibration plate and the housing.

Aspect R

In any of Aspects A through Q, the vibration plate is a metal plate including a plate face perpendicular to the direction in which the vibration plate faces the oscillation member. It is to be noted that the steps in the above-described flowchart may be executed in an order different from that in the flowchart.

Further, any one of the above-described and other example features of the present invention may be embodied in the form of an apparatus, method, system, computer program, and computer program product. For example, the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

Numerous additional modifications and variations are possible in light of the above teachings. It is therefore to be understood that, within the scope of the appended claims, the disclosure of this patent specification may be practiced otherwise than as specifically described herein.

What is claimed is:

1. A powder detector to detect an amount of powder in a powder container, the powder having flowability, the powder detector comprising:
   a vibration plate disposed in the powder container to vibrate;
   a contact member to vibrate the vibration plate; and
   a vibration detector to detect a vibration state of the vibration plate,
   wherein the vibration state of the vibration plate is affected by the powder in the powder container.

2. The powder detector according to claim 1, wherein the contact member comprises an agitator to agitate the powder in the powder container.

3. The powder detector according to claim 1, further comprising a shaft to rotate inside the powder container,
   wherein the contact member is attached to the shaft to rotate together with the shaft,
   a first end of the vibration plate in an axial direction of the shaft is secured, and
   the vibration plate includes a projection projecting toward the shaft from a second end opposite the first end, the projection pressed by the contact member.

4. The powder detector according to claim 3, wherein the projection comprises an inclined face projecting from a face of the vibration plate, the inclined face inclined to reduce a distance from the shaft along a direction of rotation of the contact member.

5. The powder detector according to claim 3, wherein the projection is different in material from the vibration plate, and
   the vibration plate including the projection has a predetermined vibration frequency.

6. The powder detector according to claim 1, further comprising:
   a frequency-related data output to output frequency-related data; and
   a detection result processor to acquire, in each predetermined sampling cycle, the frequency-related data from the frequency-related data output, wherein the vibration detector comprises a signal oscillator to output an oscillation signal having a frequency corresponding to a state of a magnetic flux passing through a space opposed to the vibration detector, the frequency-related data relates to the frequency of the oscillation signal of the signal oscillator and changes corresponding to the vibration state of the vibration plate, the vibration plate is made of a material to affect the magnetic flux and disposed facing the signal oscillator via a housing of the powder container to vibrate in a direction in which the vibration plate faces the signal oscillator, and the detection result processor detects the vibration state of the vibration plate based on a change in the frequency-related data and recognizes the amount of the powder in the powder container.

7. The powder detector according to claim 6, wherein the frequency-related data changes corresponding to an attenuation of vibration of the vibration plate vibrated by the contact member.

8. The powder detector according to claim 7, wherein the frequency-related data includes a count value of the oscillation signal output from the signal oscillator, the count value counted in the predetermined sampling cycle, and the detection result processor detects the vibration state of the vibration plate based on a change in the count value.

9. The powder detector according to claim 8, wherein the count value of the oscillation signal acquired by the detection result processor includes a first count value and a second count value counted at different timings, and the detection result processor detects the vibration state of the vibration plate based on a ratio between the first count value and the second count value.

10. The powder detector according to claim 9, wherein the detection result processor determines that the amount of the powder in the powder container is below a prescribed amount based on a comparison between a threshold and the ratio between the first count value and the second count value.

11. The powder detector according to claim 6, wherein the sampling cycle in which the detection result processor acquires the frequency-related data is shorter than a vibration cycle of the vibration plate.

12. The powder detector according to claim 6, wherein the signal oscillator comprises a coil disposed on a board to generate a magnetic flux in the direction in which the vibration plate faces the signal oscillator, and the signal oscillator outputs the oscillation signal having a frequency corresponding to an inductance of the coil.

13. An image forming apparatus comprising:
an image forming unit to form an image;
the powder container; and
the powder detector according to claim 1,
wherein the powder container contains a powder used by the image forming unit to form the image.

14. A powder detecting method to detect an amount of powder in a powder container, the powder having flowability, the powder detecting method comprising:

vibrating, using a contact member, a vibration plate disposed on the powder container;

detecting, with a vibration detector, a vibration state of the vibration plate; and recognizing the amount of the powder in the powder container according to the vibration state detected, wherein the vibration state of the vibration plate is affected by the powder in the powder container.

15. The powder detecting method according to claim 14, wherein the vibration detector comprises a signal oscillator to output an oscillation signal having a frequency corresponding to a state of a magnetic flux passing through a space opposed to the vibration detector, the vibration plate is disposed facing the signal oscillator via a housing of the powder container and to vibrate in a direction in which the vibration plate faces the signal oscillator, the vibration plate is made of a material to affect the magnetic flux, the powder detecting method further comprises:

outputting, from the signal oscillator, the oscillation signal having the frequency corresponding to the state of the magnetic flux passing through the space opposed;

acquiring, in each predetermined sampling cycle, frequency-related data that relates to the frequency of the oscillation signal of the signal oscillator and changes corresponding to the vibration state of the vibration plate;

detecting the vibration state of the vibration plate based on a change in the frequency-related data, and recognizing the amount of the powder in the powder container according to the vibration state detected.

* * * * *